United States Patent
Connolly et al.

(10) Patent No.: US 12,171,800 B2
(45) Date of Patent: Dec. 24, 2024

(54) LYOPHILIZED FORMULATION

(71) Applicant: Stemline Therapeutics, Inc., New York, NY (US)

(72) Inventors: Joan Connolly, South Orange, NJ (US); Frederick Erickson, Westerly, RI (US); Madhav Kamat, Monmouth Junction, NJ (US); Jennifer Wasserman, Hillsborough, NJ (US); James Zabrecky, Newton, MA (US)

(73) Assignee: Sterline Therapeutics, Inc., New York, NY (US)

( * ) Notice: Subject to any disclaimer, the term of this patent is extended or adjusted under 35 U.S.C. 154(b) by 0 days.

(21) Appl. No.: 18/331,318

(22) Filed: Jun. 8, 2023

(65) Prior Publication Data

US 2023/0355709 A1    Nov. 9, 2023

Related U.S. Application Data

(63) Continuation of application No. PCT/US2021/062631, filed on Dec. 9, 2021.

(60) Provisional application No. 63/123,589, filed on Dec. 10, 2020.

(51) Int. Cl.
| | | |
|---|---|---|
| A61K 38/00 | (2006.01) | |
| A61K 9/00 | (2006.01) | |
| A61K 9/08 | (2006.01) | |
| A61K 9/19 | (2006.01) | |
| A61K 38/16 | (2006.01) | |
| A61K 38/20 | (2006.01) | |
| A61K 47/26 | (2006.01) | |

(52) U.S. Cl.
CPC .......... *A61K 38/164* (2013.01); *A61K 9/0019* (2013.01); *A61K 9/08* (2013.01); *A61K 9/19* (2013.01); *A61K 38/202* (2013.01); *A61K 47/26* (2013.01)

(58) Field of Classification Search
CPC . A61K 38/202; A61K 38/164; C07K 2319/55
See application file for complete search history.

(56) References Cited

FOREIGN PATENT DOCUMENTS

| WO | WO 2006015373 | * | 2/2006 |
|---|---|---|---|
| WO | 2008030539 A2 | | 3/2008 |
| WO | 2018211517 A1 | | 11/2018 |
| WO | 2019089603 A1 | | 5/2019 |
| WO | 2020092505 A1 | | 5/2020 |

OTHER PUBLICATIONS

"Elzonris—Highlights of prescribing information", https://www.elzonris.com/ Retrieved from the Internet: URL:https://elzonris.com/hcp/resources/ELZ ONRIS_US_Full_Prescribing_Information.pdf [retrieved on Mar. 22, 2022]; 14 pages (2018).
International Search Report and Written Opinion issued in International Application No. PCT/US2021/062631 dated Mar. 30, 2022; 14 pages.
Ha et al., "Peroxide Formation in Polysorbate 8—and Protein Stability", Journal of Pharmaceutical Sciences, vol. 91, No. 10, pp. 2252-2264 (2002).

* cited by examiner

*Primary Examiner* — Gyan Chandra
(74) *Attorney, Agent, or Firm* — McNeill PLLC

(57) ABSTRACT

Provided herein are improved formulations of tagraxofusp for lyophilization used to manufacture stable formulations of tagraxofusp for intravenous injection.

28 Claims, 1 Drawing Sheet
Specification includes a Sequence Listing.

SEQUENCE LISTING

```
Sequence total quantity: 1
SEQ ID NO: 1            moltype = AA  length = 524
FEATURE                 Location/Qualifiers
REGION                  1..524
                        note = Tagraxofusp
source                  1..524
                        mol_type = protein
                        organism = synthetic construct
SEQUENCE: 1
MGADDVVDSS KSFVMENFSS YHGTKPGYVD SIQKGIQKPK SGTQGNYDDD WKGFYSTDNK  60
YDAAGYSVDN ENPLSGKAGG VVKVTYPGLT KVLALKVDNA ETIKKELGLS LTEPLMEQVG 120
TEEFIKRFGD GASRVVLSLP FAEGSSSVEY INNWEQAKAL SVELEINFET RGKRGQDAMY 180
```

```
EYMAQACAGN RVRRSVGSSL SCINLDWDVI RDKTKTKIES LKEHGPIKNK MSESPNKTVS 240
EEKAKQYLEE FHQTALEHPE LSELKTVTGT NPVFAGANYA AWAVNVAQVI DSETADNLEK 300
TTAALSILPG IGSVMGIADG AVHHNTEEIV AQSIALSSLM VAQAIPLVGE LVDIGFAAYN 360
FVESIINLFQ VVHNSYNRPA YSPGHKTRPH MAPMTQTTSL KTSWVNCSNM IDEIITHLKQ 420
PPLPLLDFNN LNGEDQDILM ENNLRRPNLE AFNRAVKSLQ NASAIESILK NLLPCLPLAT 480
AAPTRHPIHI KDGDWNEFRR KLTFYLKTLE NAQAQQTTLS LAIF                 524
```

LYOPHILIZED FORMULATION

CROSS-REFERENCE TO RELATED APPLICATIONS

This application is a continuation of International Patent Application No. PCT/US2021/62631, filed Dec. 9, 2021, which claims priority to U.S. Provisional Application No. 63/123,589, filed on Dec. 10, 2020, the disclosure of which is hereby incorporated by reference in its entirety.

FIELD

An improved lyophilized formulation of tagraxofusp with increased stability and methods of making the same.

SEQUENCE LISTING

The instant application contains a Sequence Listing which has been submitted electronically in ASCII format via EFS-Web and is hereby incorporated by reference in its entirety. Said ASCII copy, created on Dec. 7, 2021, is named 2021-12-07_01214-0022-00PCT_Seq_List_ST25.txt and is 4,806 bytes in size.

BACKGROUND

Intravenous therapy (IV) or drug delivery delivers fluids directly into a vein. The intravenous route of administration can be used both for injections, using a syringe at higher pressures; as well as for infusions, typically using only the pressure supplied by gravity (also referred to as a drip). The intravenous route delivers medications quickly throughout the body, by introduction of the therapeutic agent directly into the circulation. This direct introduction of the drug formulations into the blood stream results in 100% of the formulation being bioavailable, but that also means the formulations must be immediately compatible with the subject's physiology which limits the acceptable components within the formulation. Injectable products are sterile, pyrogen-free, and, when in solution, free of particulate matter and may be isotonic. In addition, the components must be able to withstand terminal sterilization or aseptic manufacturing processes.

Provided herein are stable pharmaceutically acceptable formulations for intravenous injection of tagraxofusp and formulations for and methods of making the same.

SUMMARY

Provided herein are stable pharmaceutically acceptable formulations for intravenous injection of tagraxofusp, as exemplified by the following non-limiting list of embodiments.

Embodiment 1 is a stable solution for lyophilization in a pharmaceutically acceptable aqueous carrier comprising:
  0.5 to 1.5 mg/mL of tagraxofusp;
  2 to 10% w/v of at least one disaccharide sugar;
  0.05 to 1.5% w/v of at least one surfactant;
  at least one 5 to 25 mM buffering agent; and a pH 6.5-9.0
  wherein the surfactant has no more than 3% peroxide.

Embodiment 2 is the lyophilization solution of embodiment 1, wherein the lyophilization solution further comprises 2 to 10% w/v of at least one bulking agent.

Embodiment 3 is the lyophilization solution of any of the preceding embodiments, comprising 0.6 to 1.4 mg/mL of tagraxofusp.

Embodiment 4 is the lyophilization solution of any of the preceding embodiments, comprising 0.7 to 1.3 mg/mL of tagraxofusp.

Embodiment 5 is the lyophilization solution of any of the preceding embodiments, comprising 0.8 to 1.2 mg/mL of tagraxofusp.

Embodiment 6 is the lyophilization solution of any of the preceding embodiments, comprising 1 mg/mL of tagraxofusp.

Embodiment 7 is the lyophilization solution of any of the preceding embodiments, wherein the surfactant is present in an amount from 0.07 to 1.5% w/v.

Embodiment 8 is the lyophilization solution of any of the preceding embodiments, wherein the surfactant is present in an amount from 0.1 to 1.3% w/v.

Embodiment 9 is the lyophilization solution of any of the preceding embodiments, wherein the surfactant is present in an amount from 0.15 to 1.2% w/v.

Embodiment 10 is the lyophilization solution of any of the preceding embodiments, wherein the surfactant is present in an amount from 0.25 to 1% w/v.

Embodiment 11 is the lyophilization solution of any of the preceding embodiments, wherein the surfactant is present in an amount from 0.24 to 0.26% w/v.

Embodiment 12 is the lyophilization solution of any of the preceding embodiments, wherein the surfactant is chosen from polysorbates or poloxamers.

Embodiment 13 is the lyophilization solution of any of the preceding embodiments, wherein the surfactant is poloxamer 188, poloxamer 168, poloxamer 144, polysorbate 20, polysorbate 60, or polysorbate 80.

Embodiment 14 is the lyophilization solution of any of the preceding embodiments, wherein the surfactant is polysorbate 80.

Embodiment 15 is the lyophilization solution of any of the preceding embodiments, wherein the disaccharide sugar is present in an amount from 2 to 8% w/v.

Embodiment 16 is the lyophilization solution of any of the preceding embodiments, wherein the disaccharide sugar is present in an amount from 2 to 6% w/v.

Embodiment 17 is the lyophilization solution of any of the preceding embodiments, wherein the disaccharide sugar is present in an amount from 2 to 4% w/v.

Embodiment 18 is the lyophilization solution of any of the preceding embodiments, wherein the disaccharide sugar is present in an amount from 2 to 3% w/v.

Embodiment 19 is the lyophilization solution of any of the preceding embodiments, wherein the disaccharide sugar is present in an amount from 2.45 to 2.55% w/v.

Embodiment 20 is the lyophilization solution of any of the preceding embodiments, wherein the disaccharide sugar is chosen from trehalose, lactose, and sucrose.

Embodiment 21 is the lyophilization solution of any of the preceding embodiments, wherein the disaccharide sugar is sucrose.

Embodiment 22 is the lyophilization solution of any of the preceding embodiments, wherein the bulking agent is present in an amount from 2 to 8% w/v.

Embodiment 23 is the lyophilization solution of any of the preceding embodiments, wherein the bulking agent is present in an amount from 2 to 6% w/v.

Embodiment 24 is the lyophilization solution of any of the preceding embodiments, wherein the bulking agent is present in an amount from 2 to 4% w/v.

Embodiment 25 is the lyophilization solution of any of the preceding embodiments, wherein the bulking agent is present in an amount from 2 to 3% w/v.

Embodiment 26 is the lyophilization solution of any of the preceding embodiments, wherein the bulking agent is present in an amount from 2.45 to 2.55% w/v.

Embodiment 27 is the lyophilization solution of any of the preceding embodiments, wherein the bulking agent is chosen from glycine, maltose, glucose, mannitol, and sorbitol.

Embodiment 28 is the lyophilization solution of any of the preceding embodiments, wherein the bulking agent is mannitol.

Embodiment 29 is the lyophilization solution of any of the preceding embodiments, wherein at least one buffering agent is at a concentration of from 5 to 15 mM.

Embodiment 30 is the lyophilization solution of any of the preceding embodiments, wherein at least one buffering agent is at a concentration of from 7 to 12 mM.

Embodiment 31 is the lyophilization solution of any of the preceding embodiments, wherein at least one buffering agent is at a concentration of 10 mM.

Embodiment 32 is the lyophilization solution of any of the preceding embodiments, wherein the buffering agent is chosen from phosphate, arginine, histidine, and Tris HCl.

Embodiment 33 is the lyophilization solution of any of the preceding embodiments, wherein the buffering agent is Tris HCl.

Embodiment 34 is the lyophilization solution of any of the preceding embodiments, wherein the pH is from 6.5 to 8.

Embodiment 35 is the lyophilization solution of any of the preceding embodiments, wherein the pH is from 7 to 8.

Embodiment 36 is a stable pharmaceutically acceptable lyophilization solution in a pharmaceutically acceptable aqueous medium comprising:
 0.5 to 1.5 mg/mL of tagraxofusp;
 2 to 10% w/v of sucrose;
 0.05 to 1.5% w/v of polysorbate 80;
 5 to 25 mM Tris HCl; and
 having a pH from 6.5 to 9;
 wherein the polysorbate 80 has no more than 3% peroxide.

Embodiment 37 is the lyophilization solution of embodiment 36, wherein the lyophilization solution further comprises 2 to 10% w/v of mannitol.

Embodiment 38 is the lyophilization solution of embodiment 36 comprising:
 1 mg/mL of tagraxofusp;
 2.45 to 2.55% w/v of sucrose;
 2.45 to 2.55% w/v of mannitol;
 0.24 to 0.26% w/v of polysorbate 80;
 9 to 11 mM Tris HCl; and
 having a pH from 6.5 to 9,
 wherein the polysorbate 80 has no more than 3% peroxide.

Embodiment 39 is a lyophile prepared from the lyophilization solution of any of the preceding embodiments.

Embodiment 40 is the lyophile of embodiment 41, wherein the relative percent abundance of an oxidized species of tagraxofusp will increase to no more than 2%, or to no more than 1%, over 12 to 36 months.

Embodiment 41 is the lyophile of embodiment 41, wherein the relative percent abundance of an oxidized species of tagraxofusp will increase to no more than 2%, or to no more than 1%, over 18 to 24 months.

Embodiment 42 is the lyophile of embodiment 41, wherein the relative percent abundance of an acidic species of tagraxofusp will increase less than the relative percent abundance of the same acidic species of tagraxofusp in a liquid tagraxofusp formulation during storage for 18, 24 or 36 months.

Embodiment 43 is the lyophile of embodiment 42, wherein the formulation provides for the required dose of 1 to 1.5 mg on dry weight basis.

Embodiment 44 is the lyophile of embodiment 42 or 43, wherein the lyophilized dry product is stable at storage temperatures from 2° C. to 8° C. for at least 24 months.

Embodiment 45 is the lyophile of any one of embodiments 42 to 44, wherein the lyophilized dry product is stable in storage temperatures from 2° C. to 8° C. for 24 months to 5 years.

Embodiment 46 is the lyophile of any one of embodiments 42 to 45, wherein an oxidation impurity is at or below 2%, or is at or below 1%, as determined by reversed-phase ultrahigh performance chromatography (RP-UPLC).

Embodiment 47 is the lyophile of any one of embodiments 42 to 46, wherein the oxidation impurity is measurable as a single peak in mass spectral analysis +16 Da from a tagraxofusp peak.

Embodiment 48 is the lyophile of any one of embodiments 42 to 47, wherein in a RP-UPLC analysis the oxidation impurity elutes before tagraxofusp and the oxidation impurity peak on the RP-UPLC chromatogram is the peak closest to the tagraxofusp peak.

Embodiment 49 is a stable lyophile comprising:
 1 mg of tagraxofusp;
 25 mg of at least one disaccharide sugar;
 25 mg of at least one surfactant; and
 2.4 mg of at least one buffering agent,
 wherein, the lyophile has no more than 2% oxidation impurity as determined by reversed-phase ultrahigh performance chromatography (RP-UPLC) for at least 24 months.

Embodiment 50 is the stable lyophile of embodiments 49, further comprising 25 mg of at least one bulking agent.

Embodiment 51 is the stable lyophile of embodiment 49 or 50, wherein the relative percent abundance of an oxidized species of tagraxofusp will increase to no more than 2%, or to no more than 1%, over 18 to 24 months.

Embodiment 52 is a method of preparing a tagraxofusp lyophile comprising:
 a) providing the lyophilization solution of any one of embodiments 1-41 and
 b) lyophilizing the solution to form a lyophile.

Embodiment 53 is the method of embodiment 52, wherein the lyophilization occurs at a temperature from −40° C. to 25° C. over a period of 2 to 7 days.

Embodiment 54 is the method of embodiment 52 or 53, wherein the lyophilization comprises a loading step, at least one freezing step, at least one annealing step, and at least one drying step.

Embodiment 55 is the method of any one of embodiments 52 to 54, wherein the lyophilization comprises a loading step, at least two freezing steps, at least two annealing steps, and at least one drying step.

Embodiment 56 is the method of any one of embodiments 52 to 55, wherein the lyophilization comprises a loading step, at least two freezing steps, and at least two annealing steps that occur over a period of no more than one day; and at least one drying step that occurs over a period of one to five days.

Embodiment 57 is the method of any one of embodiments 52 to 56, wherein the lyophilization comprises the following lyophilization cycle:
 a) loading a sample comprising the lyophilization solution into a lyophilizer, wherein the sample is pre-chilled by lowering the lyophilizer temperature to 10° C. for 10 minutes at ambient lyophilizer pressure;

b) freezing the sample in a first freezing step, wherein the temperature of the lyophilizer is changed from 10° C. to −40° C. over a period of 180 minutes at ambient lyophilizer pressure;
c) freezing the sample in a second freezing step, wherein the temperature of the lyophilizer is held at −40° C. for 60 minutes at ambient lyophilizer pressure;
d) annealing the sample in a first annealing step, wherein the temperature of the lyophilizer is changed from −40° C. to −15° C. over a period of 60 minutes at ambient lyophilizer pressure;
e) annealing the sample in a second annealing step, wherein the temperature of the lyophilizer is held at −15° C. for 60 minutes at ambient lyophilizer pressure;
f) annealing the sample in a third annealing step, wherein the temperature of the lyophilizer changes from −15° C. to −40° C. over a period of 60 minutes at ambient lyophilizer pressure;
g) annealing the sample in a fourth annealing step by holding the temperature of the lyophilizer at −40° C. for about 60 minutes at ambient lyophilizer pressure;
h) drying the sample in a first primary drying step, wherein the lyophilizer temperature is held at −40° C. and the lyophilizer pressure is held at 0.133 mBar for 10 minutes;
i) drying the sample in a second primary drying step, wherein the temperature of the lyophilizer is changed from −40° C. to −25° C. and the lyophilizer pressure is held at 0.133 mBar over a period of 60 minutes;
j) drying the sample in a third primary drying step, wherein the lyophilizer temperature is held at −25° C. and the lyophilizer pressure is held at 0.133 mBar for 2400 minutes;
k) drying the sample in a fourth primary drying step, wherein the temperature of the lyophilizer is changed from −25° C. to 25° C. and the lyophilizer pressure is held at 0.133 mBar over a period of 840 minutes; and
l) drying the sample in a secondary drying step, wherein the lyophilizer temperature is held at 25° C. and the lyophilizer pressure is held at 0.133 mBar for 1390 minutes.

Embodiment 58 is a pharmaceutically acceptable formulation reconstituted in an aqueous medium for intravenous injection comprising:
0.5 to 1.5 mg/mL of tagraxofusp;
2 to 10% w/v of at least one disaccharide sugar;
0.05 to 1.5% w/v of at least one surfactant; and
at least one 5 to 25 mM buffering agent.

Embodiment 59 is the stable lyophile of embodiment 58, wherein the relative percent abundance of an oxidized species of tagraxofusp will increase to no more than 2%, or to no more than 1%, over 18 to 24 months.

Embodiment 60 is the reconstituted formulation for intravenous injection of embodiment 58 or 59, wherein the lyophilization solution further comprises 2 to 10% w/v of at least one bulking agent.

Embodiment 61 is the reconstituted formulation for intravenous injection of any one of embodiments 58 to 60, comprising 0.5 to 1.5 mg/mL of tagraxofusp, or 0.6 to 1.4 mg/mL of tagraxofusp, or 0.7 to 1.3 mg/mL of tagraxofusp, or 0.8 to 1.2 mg/mL of tagraxofusp, or 1 mg/mL of tagraxofusp.

Embodiment 62 is the reconstituted formulation for intravenous injection of any one of embodiments 58 or 61, wherein the surfactant is present in an amount from 0.07 to 1.5% w/v, or from 0.1 to 1.3% w/v, or from 0.15 to 1.2% w/v, or from 0.25 to 1.0% w/v, or from 0.24 to 0.26% w/v.

Embodiment 63 is the reconstituted formulation for intravenous injection of any one of embodiments 58 or 62, wherein the surfactant is chosen from polysorbates or poloxamers.

Embodiment 64 is the reconstituted formulation for intravenous injection of any one of embodiments 58 to 63, wherein the the surfactant is poloxamer 188, poloxamer 168, poloxamer 144, polysorbate 20, polysorbate 60, or polysorbate 80.

Embodiment 65 is the reconstituted formulation for intravenous injection of any one of embodiments 58 to 64, wherein the surfactant is polysorbate 80.

Embodiment 66 is the reconstituted formulation for intravenous injection of any one of embodiments 58 to 65, wherein the disaccharide sugar is present in an amount from 2 to 8% w/v, or from 2 to 6% w/v, or from 2 to 4% w/v, or from 2 to 3% w/v, or from 2.45 to 2.55% w/v.

Embodiment 67 is the reconstituted formulation for intravenous injection of any one of embodiments 58 to 66, wherein the disaccharide sugar is chosen from trehalose, lactose, and sucrose.

Embodiment 68 is the reconstituted formulation for intravenous injection of any one of embodiments 58 to 67, wherein the disaccharide sugar is sucrose.

Embodiment 69 is the reconstituted formulation for intravenous injection of any one of embodiments 58 to 68, wherein the bulking agent is present in an amount from 2 to 8% w/v, or from 2 to 6% w/v, or from 2 to 4% w/v, or from 2 to 3% w/v, or from 2.45 to 2.55% w/v.

Embodiment 70 is the reconstituted formulation for intravenous injection of any one of embodiments 58 to 69, wherein the bulking agent is chosen from glycine, maltose, glucose, mannitol, and sorbitol.

Embodiment 71 is the reconstituted formulation for intravenous injection of any one of embodiments 58 to 70, wherein the bulking agent is mannitol.

Embodiment 72 is the reconstituted formulation for intravenous injection of any one of embodiments 58 to 71, wherein at least one 5 to 15 mM, or 7 to 12 mM, or 9 to 11 mM, or 10 mM, buffering agent is added.

Embodiment 73 is the reconstituted formulation for intravenous injection of any one of embodiments 58 to 72, wherein the buffering agent is chosen from phosphate, arginine, histidine, and Tris HCl.

Embodiment 74 is the reconstituted formulation for intravenous injection of any one of embodiments 58 to 73, wherein the buffering agent is Tris HCl.

Embodiment 75 is the reconstituted formulation for intravenous injection of any one of embodiments 58 to 74, wherein the pH is from 6.5 to 9.

Embodiment 76 is the reconstituted formulation for intravenous injection of any one of embodiments 58 to 75, wherein the pH is from 7 to 8.

Embodiment 77 is the reconstituted formulation for intravenous injection of any one of embodiments 58 to 76 comprising:
0.5 to 1.5 mg/mL of tagraxofusp;
2 to 10% w/v of sucrose;
0.05 to 1.5% w/v of polysorbate 80;
5 to 25 mM Tris HCl; and
having a pH from 6.5 to 9.

Embodiment 78 is the reconstituted formulation of embodiment 77, wherein the reconstituted formulation further comprises 2 to 10% w/v of mannitol.

Embodiment 79 is the reconstituted formulation for intravenous injection of any one of embodiments 58 to 78 comprising:

0.9 to 1.1 mg/mL of tagraxofusp;
2.45 to 2.55% w/v of sucrose;
2.45 to 2.55% w/v of mannitol;
0.24 to 0.26% w/v of polysorbate 80;
9 to 11 mM Tris HCl; and
having a pH from 6.5 to 9.

Embodiment 80 is the reconstituted formulation for intravenous injection of any one of embodiments 58 to 79, wherein the aqueous medium is water for injection (WFI).

Embodiment 81 is the reconstituted formulation for intravenous injection of any one of embodiments 58 to 80, which upon dilution into an infusion fluid bag provides a fluid in the infusion fluid bag that is substantially free of particulate matter.

Embodiment 82 is the reconstituted formulation for intravenous injection of Embodiment 81, wherein the infusion fluid bag is a 50 cc infusion bag.

Embodiment 83 is the reconstituted formulation for intravenous injection of any one of embodiments 58 to 82, which upon dilution into an infusion fluid bag provides a fluid in the infusion fluid bag that is substantially free of particulate matter and further wherein the fluid in the infusion fluid bag comprises normal saline or Dextrose 5% (w/v).

Embodiment 84 is a method for treating a myeloproliferative neoplasm (MPN) with monocytosis, comprising administering to a subject in need thereof an effective amount of the reconstituted formulation for intravenous injection of any one of embodiments 58 to 83.

Embodiment 85 is a method for treating a myeloproliferative neoplasm (MPN), wherein the MPN is polycythemia vera (PV), essential thrombocythemia (ET), myelofibrosis (MF), chronic myelomonocytic leukemia (CMML), chronic neutrophilic leukemia, chronic eosinophilic leukemia, systemic mastocytosis (SM), symptomatic hypereosinophilic disorder, or other bone marrow disorder that causes the production of excess red blood cells, white blood cells, and/or platelets, or a primary eosinophilic disorder (PED), comprising administering to a subject in need thereof an effective amount of the reconstituted formulation for intravenous injection of any one of embodiments 58 to 83.

Embodiment 86 is a method for treating acute myeloid leukemia (AML), comprising administering to a subject in need thereof an effective amount of the reconstituted formulation for intravenous injection of any one of embodiments 58 to 83.

Embodiment 87 is a method for treating chronic myelomonocytic leukemia (CMML) comprising administering to a subject in need thereof an effective amount of the reconstituted formulation for intravenous injection of any one of embodiments 58 to 78.

Embodiment 88 is a method for treating myelodysplastic syndrome (MDS) comprising administering to a subject in need thereof an effective amount of the reconstituted formulation for intravenous injection of any one of embodiments 58 to 83.

Embodiment 89 is a method for treating multiple myeloma in a subject in need thereof, comprising administering to the subject in need thereof an effective amount of the reconstituted formulation for intravenous injection of any one of embodiments 58 to 83.

Embodiment 90 is a method for treating blastic plasmacytoid dendritic cell neoplasm (BPDCN) comprising administering to a subject in need thereof an effective amount of the reconstituted formulation for intravenous injection of any one of embodiments 58 to 83.

Embodiment 91 is a method of treating an autoimmune disease comprising administering to a subject in need thereof an effective amount of the reconstituted formulation for intravenous injection of any one of embodiments 58 to 83.

Embodiment 92 is the method embodiment 91, wherein the autoimmune disease is chosen from lupus (e.g., systemic lupus erythematosus, cutaneous lupus, discoid lupus), Sjogren's syndrome, inflammatory arthritis, systemic sclerosis (SSc), morphea, psoriasis, lichen planus, dermatomyositis, lichen sclerosus, and cutaneous graft-versus-host disease (GVHD), adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dense deposit disease, essential mixed cryoglobulinemia, fibromyalgia-fibromyositis, glomerulonephritis (e.g., IgA nephropathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, Ménière's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychondritis, polyendocrinopathies, polyglandular syndromes, polymyalgia rheumatica, polymyositis, post-MI, primary agammaglobulinemia, primary biliary cirrhosis, psoriatic arthritis, Raynaud's phenomenon, relapsing polychondritis, Reiter's syndrome, rheumatic heart disease, rheumatoid arthritis, sarcoidosis, stiff-man syndrome, takayasu arteritis, temporal arteritis/giant cell arteritis, ulcerative colitis, urticaria, uveitis, Uveitis Ophthalmia, vasculitides such as dermatitis herpetiformis vasculitis, vitiligo, and Wegener's granulomatosis.

Embodiment 93 is a method for treating or inhibiting solid tumors comprising administering to a subject in need thereof an effective amount of the reconstituted formulation for intravenous injection of any one of embodiments 58 to 83.

Embodiment 94 is the method of embodiment 93, wherein the solid tumor is chosen from sarcomas, carcinomas, and lymphomas.

Embodiment 95 is the method of any of embodiments 84 to 94, wherein tagraxofusp is administered at a dose of 4 µg/kg to 20 µg/kg.

Embodiment 96 is the method of any of embodiments 84 to 94, wherein tagraxofusp is administered at a dose of 6 µg/kg to 16 µg/kg.

Embodiment 97 is the method of any of embodiments 84 to 94, wherein tagraxofusp is administered at a dose of 7 µg/kg.

Embodiment 98 is the method of any of embodiments 84 to 94, wherein tagraxofusp is administered at a dose of 9 µg/kg.

Embodiment 99 is the method of any of embodiments 84 to 94, wherein tagraxofusp is administered at a dose of 12 µg/kg.

Embodiment 100 is the method of any one of embodiments 84 to 94, wherein tagraxofusp is administered at a dose of 12 μg/kg over 15 minutes.

Embodiment 101 is the method of any of embodiments 84 to 100, wherein tagraxofusp is administered at a dose that is the maximum tolerated dose.

Embodiment 102 is the method of any of embodiments 84 to 101, wherein tagraxofusp is administered once every day for five days.

Embodiment 103 is the method of any of embodiments 84 to 101, wherein tagraxofusp is administered once every day for three days.

Embodiment 104 is the method of any of embodiments 84 to 103, wherein tagraxofusp is administered for multiple cycles.

Embodiment 105 is the method of any one of embodiments 84 to 102, wherein tagraxofusp is administered on days 1 to 5 of a 21-day cycle.

Embodiment 106 is the method of any one of embodiments 84 to 102, wherein tagraxofusp is administered on days 1 to 5 of a 28-day cycle.

Embodiment 107 is the method of any one of embodiments 84 to 101, and 103, wherein tagraxofusp is administered on days 1 to 3 of a 21-day cycle.

Embodiment 108 is the method of any one of embodiments 84 to 101, wherein tagraxofusp is administered for 5 days during any one of the first 10 days of a 21-day cycle.

Embodiment 109 is the stable pharmaceutically acceptable lyophilization solution of any one of embodiments 1-41 in a vial.

Embodiment 110 is the stable pharmaceutically acceptable lyophilization solution of embodiment 38 or 40 in a vial.

Embodiment 111 is the lyophile of any one of embodiments 42 to 51 in a vial.

Embodiment 112 is the lyophile of embodiment 49 or 50 in a vial.

Embodiment 113 is the lyophile of embodiment 111 or 112 containing water.

Embodiment 114 is a vial containing a reconstituted solution of any one of embodiments 58 to 80.

Embodiment 115 is a vial containing a reconstituted solution of any one of embodiments 58, 60, 77, or 79.

Embodiment 116 is the solution, lyophile or vial of any one of embodiments 109-115 wherein the vial is a 2 mL or a 3 mL vial.

Embodiment 117 is a stable solution for lyophilization in a pharmaceutically acceptable aqueous carrier comprising:
  0.5 to 1.5 mg/mL of tagraxofusp;
  2 to 10% w/v of at least one disaccharide sugar;
  0.05 to 1.5% w/v of at least one surfactant;
  at least one 5 to 25 mM buffering agent; and a pH 6.5-9.0
  wherein the surfactant has no more than 3% peroxide.

Embodiment 118 is the lyophilization solution of embodiment 117, wherein the lyophilization solution further comprises 2 to 10% w/v of at least one bulking agent.

Embodiment 119 is the lyophilization solution of embodiment 117 or 118, comprising 0.6 to 1.4 mg/mL of tagraxofusp, or, 0.7 to 1.3 mg/mL of tagraxofusp, or 0.8 to 1.2 mg/mL of tagraxofusp, or 1 mg/mL of tagraxofusp.

Embodiment 120 is the lyophilization solution of any one of embodiments 117 to 119, wherein the surfactant is present in an amount from 0.07 to 1.5% w/v, or from 0.1 to 1.3% w/v, or from 0.15 to 1.2% w/v, or from 0.25 to 1% w/v, or from 0.24 to 0.26% w/v.

Embodiment 121 is the lyophilization solution of any one of embodiments 117 to 120, wherein the surfactant is chosen from polysorbates or poloxamers, or wherein the surfactant is poloxamer 188, poloxamer 168, poloxamer 144, polysorbate 20, polysorbate 60, or polysorbate 80, or wherein the surfactant is polysorbate 80.

Embodiment 122 is the lyophilization solution of any one of embodiments 117 to 121, wherein the disaccharide sugar is present in an amount from 2 to 8% w/v, or 2 to 6% w/v, or 2 to 4% w/v, or 2 to 3% w/v, or 2.45 to 2.55% w/v.

Embodiment 123 is the lyophilization solution of any one of embodiments 117 to 122, wherein the disaccharide sugar is chosen from trehalose, lactose, and sucrose, or wherein the disaccharide sugar is sucrose.

Embodiment 124 is the lyophilization solution of any one of embodiments 117 to 123, wherein the bulking agent is present in an amount from 2 to 8% w/v, or from 2 to 6% w/v, or 2 to 4% w/v, or 2 to 3% w/v, or 2.45 to 2.55% w/v.

Embodiment 125 is the lyophilization solution of any one of embodiments 117 to 124, wherein the bulking agent is chosen from glycine, maltose, glucose, mannitol, and sorbitol, or wherein the bulking agent is mannitol.

Embodiment 126 is the lyophilization solution of any one of embodiments 117 to 125, wherein at least one buffering agent is at a concentration of from 5 to 15 mM, or from 7 to 12 mM, or 10 mM.

Embodiment 127 is the lyophilization solution of any one of embodiments 117 to 126, wherein the buffering agent is chosen from phosphate, arginine, histidine, and Tris HCl, or wherein the buffering agent is Tris HCl.

Embodiment 128 is the lyophilization solution of any one of embodiments 117 to 127, wherein the pH is from 6.5 to 8, or wherein the pH is from 7 to 8.

Embodiment 129 is a stable pharmaceutically acceptable lyophilization solution in a pharmaceutically acceptable aqueous medium comprising:
  0.5 to 1.5 mg/mL of tagraxofusp;
  2 to 10% w/v of sucrose;
  0.05 to 1.5% w/v of polysorbate 80;
  5 to 25 mM Tris HCl; and
  having a pH from 6.5 to 9;
  wherein the polysorbate 80 has no more than 3% peroxide.

Embodiment 130 is the lyophilization solution of embodiment 129, wherein the lyophilization solution further comprises 2 to 10% w/v of mannitol.

Embodiment 131 is the lyophilization solution of embodiment 130 comprising:
  1 mg/mL of tagraxofusp;
  2.45 to 2.55% w/v of sucrose;
  2.45 to 2.55% w/v of mannitol;
  0.24 to 0.26% w/v of polysorbate 80;
  9 to 11 mM Tris HCl; and
  having a pH from 6.5 to 9,
  wherein the polysorbate 80 has no more than 3% peroxide.

Embodiment 132 is a lyophile prepared from the lyophilization solution of any one of embodiments 117 to 131.

Embodiment 133 is the lyophile of embodiment 132, wherein:
  (a) the relative percent abundance of an oxidized species of tagraxofusp will increase to no more than 2%, or to no more than 1%, over 12 to 36 months, or wherein the relative percent abundance of an oxidized species of tagraxofusp will increase to no more than 2%, or to no more than 1%, over 18 to 24 months;
  (b) the relative percent abundance of an acidic species of tagraxofusp will increase less than the relative percent abundance of the same acidic species of tagraxofusp in a liquid tagraxofusp formulation during storage for 18, 24 or 36 months;

(c) the formulation provides for the required dose of 1 to 1.5 mg on dry weight basis;

(d) the lyophilized dry product is stable at storage temperatures from 2° C. to 8° C. for at least 24 months, or wherein the lyophilized dry product is stable in storage temperatures from 2° C. to 8° C. for 24 months to 5 years; and/or (e) an oxidation impurity is at or below 2%, or is at or below 1%, as determined by reversed-phase ultrahigh performance chromatography (RP-UPLC), and/or wherein the oxidation impurity is measurable as a single peak in mass spectral analysis +16 Da from a tagraxofusp peak, and/or wherein in a RP-UPLC analysis the oxidation impurity elutes before tagraxofusp and the oxidation impurity peak on the RP-UPLC chromatogram is the peak closest to the tagraxofusp peak.

Embodiment 134 is a stable lyophile comprising:

1 mg of tagraxofusp;

25 mg of at least one disaccharide sugar;

25 mg of at least one surfactant; and 2.4 mg of at least one buffering agent, wherein, the lyophile has no more than 2% oxidation impurity as determined by reversed-phase ultrahigh performance chromatography (RP-UPLC) for at least 24 months.

Embodiment 135 is the stable lyophile of embodiment 134, (a) further comprising 25 mg of at least one bulking agent;

(b) wherein the relative percent abundance of an oxidized species of tagraxofusp will increase to no more than 2%, or to no more than 1%, over 18 to 24 months Embodiment 136 is a method of preparing a tagraxofusp lyophile comprising:

a) providing the lyophilization solution of any one of embodiments 117 to 131 and b) lyophilizing the solution to form a lyophile.

Embodiment 137 is the method of embodiment 136, wherein the lyophilization occurs at a temperature from 40° C. to 25° C. over a period of 2 to 7 days, and/or wherein the lyophilization comprises a loading step, at least one freezing step, at least one annealing step, and at least one drying step, and/or wherein the lyophilization comprises a loading step, at least two freezing steps, at least two annealing steps, and at least one drying step, and/or wherein the lyophilization comprises a loading step, at least two freezing steps, and at least two annealing steps that occur over a period of no more than one day; and at least one drying step that occurs over a period of one to five days.

Embodiment 138 is the method of embodiment 136 or 137, wherein the lyophilization comprises the following lyophilization cycle:

a) loading a sample comprising the lyophilization solution into a lyophilizer, wherein the sample is pre-chilled by lowering the lyophilizer temperature to 10° C. for 10 minutes at ambient lyophilizer pressure;

b) freezing the sample in a first freezing step, wherein the temperature of the lyophilizer is changed from 10° C. to −40° C. over a period of 180 minutes at ambient lyophilizer pressure;

c) freezing the sample in a second freezing step, wherein the temperature of the lyophilizer is held at 40° C. for 60 minutes at ambient lyophilizer pressure;

d) annealing the sample in a first annealing step, wherein the temperature of the lyophilizer is changed from 40° C. to −15° C. over a period of 60 minutes at ambient lyophilizer pressure;

e) annealing the sample in a second annealing step, wherein the temperature of the lyophilizer is held at −15° C. for 60 minutes at ambient lyophilizer pressure;

f) annealing the sample in a third annealing step, wherein the temperature of the lyophilizer changes from 15° C. to −40° C. over a period of 60 minutes at ambient lyophilizer pressure;

g) annealing the sample in a fourth annealing step by holding the temperature of the lyophilizer at 40° C. for about 60 minutes at ambient lyophilizer pressure;

h) drying the sample in a first primary drying step, wherein the lyophilizer temperature is held at 40° C. and the lyophilizer pressure is held at 0.133 mBar for 10 minutes;

i) drying the sample in a second primary drying step, wherein the temperature of the lyophilizer is changed from 40° C. to −25° C. and the lyophilizer pressure is held at 0.133 mBar over a period of 60 minutes;

j) drying the sample in a third primary drying step, wherein the lyophilizer temperature is held at −25° C. and the lyophilizer pressure is held at 0.133 mBar for 2400 minutes;

k) drying the sample in a fourth primary drying step, wherein the temperature of the lyophilizer is changed from 25° C. to 25° C. and the lyophilizer pressure is held at 0.133 mBar over a period of 840 minutes; and l) drying the sample in a secondary drying step, wherein the lyophilizer temperature is held at 25° C. and the lyophilizer pressure is held at 0.133 mBar for 1390 minutes.

Embodiment 139 is a pharmaceutically acceptable formulation reconstituted in an aqueous medium for intravenous injection comprising:

0.5 to 1.5 mg/mL of tagraxofusp;

2 to 10% w/v of at least one disaccharide sugar;

0.05 to 1.5% w/v of at least one surfactant; and at least one 5 to 25 mM buffering agent.

Embodiment 140 is the reconstituted formulation for intravenous injection of embodiment 139, (a) the relative percent abundance of an oxidized species of tagraxofusp will increase to no more than 2%, or to no more than 1%, over 18 to 24 months;

(b) the lyophilization solution further comprises 2 to 10% w/v of at least one bulking agent;

(c) the formulation comprises 0.5 to 1.5 mg/mL of tagraxofusp, or 0.6 to 1.4 mg/mL of tagraxofusp, or 0.7 to 1.3 mg/mL of tagraxofusp, 0.8 to 1.2 mg/mL of tagraxofusp, or 1 mg/mL of tagraxofusp;

(d) the surfactant is present in an amount from 0.07 to 1.5% w/v, or from 0.1 to 1.3% w/v, or from 0.15 to 1.2% w/v, or from 0.25 to 1.0% w/v, or from 0.24 to 0.26% w/v;

(e) the surfactant is chosen from polysorbates or poloxamers, or wherein the surfactant is poloxamer 188, poloxamer 168, poloxamer 144, polysorbate 20, polysorbate 60, or polysorbate 80, or wherein the surfactant is polysorbate 80;

(f) the disaccharide sugar is present in an amount from 2 to 8% w/v, or from 2 to 6% w/v, or from 2 to 4% w/v, or from 2 to 3% w/v, or from 2.45 to 2.55% w/v;

(g) the disaccharide sugar is chosen from trehalose, lactose, and sucrose, or wherein the disaccharide sugar is sucrose;

(h) the bulking agent is present in an amount from 2 to 8% w/v, or from 2 to 6% w/v, or from 2 to 4% w/v, or from 2 to 3% w/v, or from 2.45 to 2.55% w/v; (i) the bulking agent is chosen from glycine, maltose, glucose, mannitol, and sorbitol, or wherein the bulking agent is mannitol;

(j) at least one 5 to 15 mM, or 7 to 12 mM, or 9 to 11 mM, or 10 mM, buffering agent is added;

(k) the buffering agent is chosen from phosphate, arginine, histidine, and Tris HCl, or wherein the buffering agent is Tris HCl; and/or (l) the pH is from 6.5 to 9, or wherein the pH is from 7 to 8.

Embodiment 141 is the reconstituted formulation for intravenous injection of embodiment 139 or 140 comprising:

0.5 to 1.5 mg/mL of tagraxofusp;
2 to 10% w/v of sucrose;
0.05 to 1.5% w/v of polysorbate 80;
5 to 25 mM Tris HCl; and
having a pH from 6.5 to 9,
wherein the aqueous medium is water for injection (WFI).

Embodiment 142 is the reconstituted formulation of embodiment 141, wherein the reconstituted formulation further comprises 2 to 10% w/v of mannitol.

Embodiment 143 is the reconstituted formulation for intravenous injection of any one of embodiments 139 to 142 comprising:

0.9 to 1.1 mg/mL of tagraxofusp;
2.45 to 2.55% w/v of sucrose;
2.45 to 2.55% w/v of mannitol;
0.24 to 0.26% w/v of polysorbate 80;
9 to 11 mM Tris HCl; and
having a pH from 6.5 to 9.

Embodiment 144 is the reconstituted formulation for intravenous injection of any one of embodiments 139 to 143, which upon dilution into an infusion fluid bag provides a fluid in the infusion fluid bag that is substantially free of particulate matter.

Embodiment 145 is a method for treating a disease comprising administering to a subject in need thereof an effective amount of the reconstituted formulation for intravenous injection of any one of embodiments 139 to 144, wherein the disease is a) a myeloproliferative neoplasm (MPN) with monocytosis, b) a myeloproliferative neoplasm (MPN), wherein the MPN is polycythemia vera (PV), essential thrombocythemia (ET), myelofibrosis (MF), chronic myelomonocytic leukemia (CMML), chronic neutrophilic leukemia, chronic eosinophilic leukemia, systemic mastocytosis (SM), symptomatic hypereosinophilic disorder, or other bone marrow disorder that causes the production of excess red blood cells, white blood cells, and/or platelets, or a primary eosinophilic disorder (PED)

c) acute myeloid leukemia (AML), d) chronic myelomonocytic leukemia (CMML), e) myelodysplastic syndrome (MDS), f) multiple myeloma, g) blastic plasmacytoid dendritic cell neoplasm (BPDCN), h) an autoimmune disease, i) an autoimmune disease, wherein the autoimmune disease is chosen from lupus (e.g., systemic lupus erythematosus, cutaneous lupus, discoid lupus), Sjogren's syndrome, inflammatory arthritis, systemic sclerosis (SSc), morphea, psoriasis, lichen planus, dermatomyositis, lichen sclerosus, and cutaneous graft-versus-host disease (GVHD), adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dense deposit disease, essential mixed cryoglobulinemia, fibromyalgia-fibromyositis, glomerulonephritis (e.g., IgA nephropathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, Ménière's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychondritis, polyendocrinopathies, polyglandular syndromes, polymyalgia rheumatica, polymyositis, post-MI, primary agammaglobulinemia, primary biliary cirrhosis, psoriatic arthritis, Raynaud's phenomenon, relapsing polychondritis, Reiter's syndrome, rheumatic heart disease, rheumatoid arthritis, sarcoidosis, stiff-man syndrome, takayasu arteritis, temporal arteritis/giant cell arteritis, ulcerative colitis, urticaria, uveitis, Uveitis Ophthalmia, vasculitides such as dermatitis herpetiformis vasculitis, vitiligo, and Wegener's granulomatosis Embodiment 146 is a method for treating or inhibiting solid tumors comprising administering to a subject in need thereof an effective amount of the reconstituted formulation for intravenous injection of any one of embodiments 139 to 144, optionally wherein the solid tumor is chosen from sarcomas, carcinomas, and lymphomas.

Embodiment 147 is the stable pharmaceutically acceptable lyophilization solution of any one of embodiments 117 to 131 in a vial.

Embodiment 148 is the lyophile of any one of embodiments 132 to 135 in a vial.

Embodiment 149 is a vial containing a reconstituted solution of any one of embodiments 139 to 144.

Embodiment 150 is the solution, lyophile or vial of any one of embodiments 147 to 149 wherein the vial is a 2 mL or a 3 mL vial.

DETAILED DESCRIPTION

I. Definitions

Figure 1A:
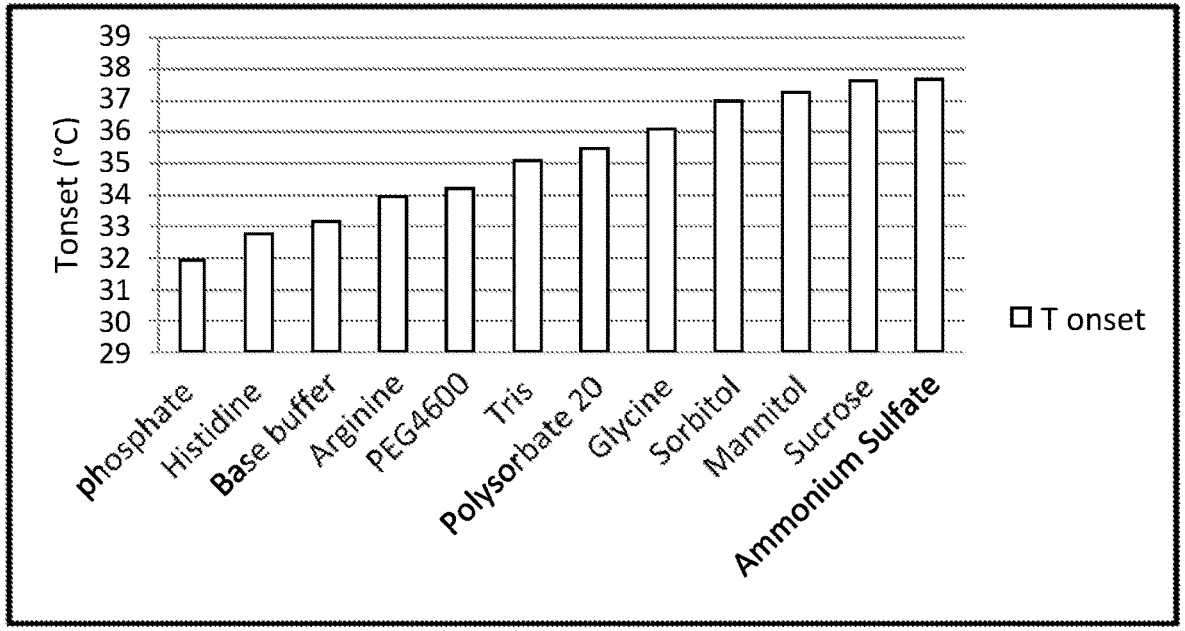
FIG. 1A provides DSC Data from the evaluations of stabilizing excipient detailed in Example 2.

As used herein, the terms "administering" and "administered" refer to the delivery of a composition into a subject by a method or route that results in at least partial localization of the composition at a desired site. A composition can be administered by any appropriate route that results in effective treatment in the subject, i.e., administration results in delivery to a desired location in the subject where at least a portion of the composition is delivered to the desired site for a period of time. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In some examples, the route is intravenous.

As used herein, the term "agent" refers to any molecule, compound, and/or substance for use in the prevention, treatment, management and/or diagnosis of a disease, including the tagraxofusp disclosed herein.

As used herein, the term "buffer" or "buffering agent" refers to one or more components that can protect the variation in solution pH when added to an aqueous solution, when an acid or alkali is added, or diluted with a solvent. In addition to phosphate buffer, glycinate, carbonate, citrate buffer, etc. can be used, in which case sodium, potassium or ammonium ions can function as counterions.

As used herein, the term "bulking agent" refers to one or more components that forms the bulk of the lyophilized product and provide an adequate structure to the cake. These are generally used for low dose (high potency) drugs that do not have the necessary bulk to support their own structure.

As used herein, the term "carrier" refers to a diluent, adjuvant or excipient, with which a composition disclosed herein is administered. In some embodiments, carriers are sterile. Water may be a carrier. Saline solutions and aqueous dextrose and glycerol solutions can also be employed as liquid carriers.

As used herein, the term "charge variant profile" refers to relative amounts of various species of the protein that differ in net charge. Proteins are large molecules that contain numerous chemical entities that are susceptible to a variety of post-translational enzymatic and chemical modifications that can change the overall charge of the molecule. In addition, chemical modifications such as oxidation or deamination can occur during the manufacturing process and storage. The charge state can impact the structure, stability, binding affinity, efficacy and safety of the biotherapeutic drug. The analysis of charged variants is usually a regulatory requirement for bio-therapeutic proteins and can be accomplished using isoelectric focusing or Ion Exchange Chromatography. Changes in the relative amounts of various charge variants due to process inconsistencies and/or stability-related events can adversely impact the safety and efficacy of a biotherapeutic protein.

As used herein, the term "excipient" refers to substances used to formulate therapeutic agents into pharmaceutical formulations and may be any solid, liquid, semi-solid additives such as diluents, solubilizing agents, stabilizers, adjuvants, thickeners, lubricating agents, bulking agents, buffers, tonicifying agents, antimicrobial agents, wetting agents, and surfactants.

As used herein, the term "effective amount" or "amount sufficient" refers to the amount of a therapeutic composition or therapy that is sufficient to result in the prevention of the development, recurrence, or onset of a disease or disorder and one or more symptoms thereof, to reduce the severity or duration of a disease or disorder, to ameliorate one or more symptoms of a disease or disorder, to prevent the advancement of a disease or disorder, to cause regression of a disease or disorder, and/or to enhance or improve the therapeutic effect(s) of another therapy. In an embodiment, the "effective amount" or "therapeutically effective amount" refers to the amount of a composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. In a specific embodiment, a therapeutic composition in an "amount sufficient" refers to the amount of the composition needed to prevent, reduce, or alleviate at least one or more signs or symptoms of a disease. The term "effective amount" therefore refers to an amount of a composition that is sufficient to promote a particular effect when administered to a typical subject, such as one who has or is at risk for cancer or, for example, an autoimmune disease. An effective amount would also include an amount sufficient to delay the development of a symptom of the disease, alter the course of a symptom of the disease (for example, but not limited to, slow the progression of a symptom of the disease), or reverse a symptom of the disease. It is understood that for any given case, an appropriate "effective amount" can be determined by one of ordinary skill in the art using routine experimentation.

As used herein, the term "isotonic" refers to a formulation having essentially the same osmotic pressure as human blood. Isotonic formulations will generally have an osmotic pressure from 250 to 350 mOsmol/KgH$_2$O. Isotonicity can be measured, for example, using a vapor pressure or ice-freezing type osmometer.

As used herein, the terms "lyophilization" and "lyophilized," refer to a process by which the material to be dried is first frozen and then the ice or frozen solvent is removed by sublimation in a vacuum environment.

As used herein, the term "lyophilization solution" refers to a formulation to be subjected to a lyophilization process.

As used herein, the term "lyophile" refers to any solid material obtained by lyophilization of a lyophilization solution, i.e., freeze-drying of an aqueous solution.

As used herein, the term "lyoprotectant" refers to a molecule that, when combined with a protein of interest, prevents or reduces the chemical and/or physical instability of the protein before and during lyophilization, or freeze-drying, and during subsequent storage. Lyoprotection is defined as the stabilization and prevention of the degradation of the therapeutic agent both during freeze-drying and afterwards.

As used herein, the terms "manage," "managing," and "management" in the context of the administration of a therapy to a subject refer to the beneficial effects that a subject derives from a therapy (e.g., a prophylactic or therapeutic composition) or a combination of therapies, while not resulting in a cure of the disease or disorder. In certain embodiments, a subject is administered one or more therapies (e.g., one or more prophylactic or therapeutic compositions) to "manage" a disease so as to prevent the progression or worsening of the condition.

As used herein, the term "peroxide" or "peroxides" refers to any of a class of chemical compounds in which two oxygen atoms are linked together by a single covalent bond. Organic peroxides, are compounds with the linkage C—O—O—C or C—O—O—H. One example is tert-butylhydroperoxide. Peroxides are known to easily decompose into highly reactive free radical containing moieties (C—O· or H—O·) that can cause further degradation or destabilize pharmaceutical formulations.

As used herein, the term "pharmaceutically acceptable," refers to compounds, materials, compositions, formulations and/or dosage forms which are, within the scope of sound medical judgment, suitable for use in contact with the tissues of subjects, human beings or other animals, without excessive toxicity, irritation, allergic response or other problem or complication commensurate with a reasonable benefit/risk ratio.

As used herein, the terms "prevent," "preventing" and "prevention" in the context of the administration of a therapy to a subject refer to the prevention or inhibition of the recurrence, onset, and/or development of a disease or disorder, or a symptom thereof in a subject resulting from the administration of a therapy (e.g., a prophylactic or therapeutic agent), or a combination of therapies (e.g., a combination of prophylactic or therapeutic agents). In certain embodiments, such terms refer to one, two, three, or more results following the administration of one or more therapies: (1) a delay in the development of a symptom of the disease, (2) an alteration of the course of a symptom of the disease (for example, but not limited to, slowing the progression of a symptom of the disease), (3) a reversal of a symptom of the disease, (4) a decrease in the recurrence rate of the disease, (5) an increase in the time to recurrence of the disease, (6) an increase in the disease-free, relapse-free, progression-free, and/or overall survival of the patient, and (7) an amelioration of disease-related symptoms and/or quality of life. In certain embodiments, such terms refer to a reduction in mortality and/or an increase in survival rate of a patient population. In further embodiments, such terms refer to an increase or enhancement in the quality of life of a patient population. In certain embodiments, such terms refer to a decrease in hospitalization rate of a patient population and/or a decrease in hospitalization length for a patient population.

As used herein, the term "reconstituted" or "reconstituted formulation" refers to a formulation prepared by dissolving a lyophile in an aqueous carrier. In some embodiments, a reconstituted formulation is suitable for intravenous injection (IV) in patients in need thereof.

As used herein, the term "stable" refers to a formulation or composition in which the therapeutic agent contained therein inherently retains its physical and chemical stability and integrity during processing and storage. The stability of a formulation can be measured at a selected temperature after a selected period. For example, increased particulates, aggregate formation or presence of other impurities after lyophilization and storage is an indication of the instability of a lyophilized formulation. In addition to aggregate formation, retention of the original clarity, color and odor throughout the shelf life is an indicator that can be used to monitor the stability solutions.

As used herein, the terms "subject" and "patient," used interchangeably, refer to a human subject, although it is to be understood that the methods described herein are effective with respect to all vertebrate species which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In certain embodiments, the subject is a human such as an infant, a juvenile, or an adult. Further, a "subject" can include a patient afflicted with or suspected of being afflicted with a condition or disease.

As used herein, the term "surfactant" is a surface-active molecule that contains both hydrophobic moieties (e.g., alkyl chains) and hydrophilic moieties (e.g., carboxyl and carboxylic acid groups). Surfactants can be added to the formulations disclosed herein. Surfactants suitable for use in the formulations herein include, but are not limited to, polysorbates (e.g., polysorbate 20, 60 or 80); poloxamers (e.g., poloxamer 144, 168 or 188); sorbitan esters and derivatives; Triton Sodium lauryl sulfate; sodium octylglycoside; lauryl-, myristyl-, linoleyl-, or stearyl-sulfobetamine; lauryl-, myristyl-, linoleyl-, or stearyl-sarcosine; linoleyl-, myristyl-, or cetyl-betaine; lauroamide Propyl-, cocamidopropyl-, linoleamidopropyl-, myrisamidopropyl-, palmidopropyl-, or isosteramidopropylbetaine (e.g., lauroamidopropyl); myrisamide propi Ru-, palmidopropyl-, or isosteramidopropyl-dimethylamine; methyl cocoyltaurate sodium or methyl oleyl-taurate disodium; and the MONAQUAT™ series (Mona Industries, Inc., Patterson, NJ), polyethylene glycol, Polypropyl glycol, and copolymers of ethylene glycol and propylene glycol (e.g., Pluronics, PF68, etc.).

As used herein, the terms "therapies" and "therapy" can refer to any method(s), composition(s), and/or agent(s) that can be used in the prevention, treatment and/or management of a disease, disorder or condition, or one or more symptoms thereof. In certain embodiments, the terms "therapy" and "therapies" refer to steroid therapy, physical therapy, gene therapy, chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or a combination of the foregoing and/or other therapies useful in the prevention, management and/or treatment of a disease, disorder or condition, or one or more symptoms thereof.

As used herein, the terms "treat," "treatment," and "treating" in the context of the administration of a therapeutic composition to a subject refer to the reversal, reduction or inhibition of the progression and/or duration of the disease, preventing or reducing the likelihood of the disease, reduction or amelioration of the severity, and/or the amelioration of one or more symptoms of the disease, disorder, or condition to which such term applies resulting from the administration of one or more therapies.

II. Improved Formulations

ELZONRIS® is a CD123-directed cytotoxin currently approved for use in the United States for the treatment of blastic plasmacytoid dendritic cell neoplasm (BPDCN) in adults and in pediatric patients 2 years and older. ELZONRIS® is a commercial formulation of the therapeutic agent tagraxofusp (marketed in the US under the generic name tagroxofusp-erzs). Tagraxofusp is a diphtheria toxin-IL-3 fusion protein targeting the IL-3 receptor and can be found in the DrugBank using accession number DB14731 and is described in U.S. Pat. Nos. 7,763,242; 8,470,307; 9,181,317; 9,631,006; and 10,259,853.

Embodiments disclosed herein provide a stable pharmaceutically acceptable lyophilization solution including 0.5 to 1.5 mg/mL of tagraxofusp. In other embodiments the lyophilization solution includes 0.6 to 1.4 mg/mL of tagraxofusp. In other embodiments the lyophilization solution includes 0.7 to 1.3 mg/mL of tagraxofusp. In other embodiments the lyophilization solution includes 0.8 to 1.2 mg/mL of tagraxofusp. In other embodiments the lyophilization solution includes 0.9 to 1.1 mg/mL of tagraxofusp. In other embodiments the lyophilization solution includes 1 mg/mL of tagraxofusp. Embodiments disclosed herein provide a stable pharmaceutically acceptable lyophilization solution including 1 mg/vial of tagraxofusp. In other embodiments the lyophilization solution includes 1.5 mg/vial of tagraxofusp.

Embodiments disclosed herein provide a stable pharmaceutically acceptable lyophilization solution that contains lower levels of charge variants over the course of its shelf life compared to formulations that are not lyophilized according to the formulations and methods described herein. In some embodiments, the charge variant profile can be determined or approximated based on the amount of the measured acidic species impurities. In some embodiments the relative percent abundance of an acidic species impurity will increase during storage of the tagraxofusp drug product. In some embodiments, the reported value for relative percent abundance of an acidic species impurity will increase by 3 to 8 percentage points in a liquid product formulation of tagraxofusp, while the relative percent abundance of the same acidic species impurity will increase from 0 to 2, or from 0 to 1, or from 0 to 0.5 percentage points in the lyophile drug product formulations as described herein. In some embodiments the drug product is stored for 12, 18, 24 or 36 months. In some embodiments the drug product is stored for 24 months. In some embodiments, the relative percent abundance of an acidic species of tagraxofusp, in the lyophile as described herein, will increase less than the relative percent abundance of the same acidic species of tagraxofusp in a liquid tagraxofusp formulation during storage for 18, 24 or 36 months.

Without wishing to be bound by theory, it is believed that judicious choice of surfactant type and purity used in the preparation of the lyophilization solution may prevent particulate and/or impurity formation during manufacturing, during storage throughout the shelf life, as well as during the processes of reconstitution and administration to the patient.

In some embodiments, the lyophilization solution includes tagraxofusp, at least one disaccharide sugar, at least one surfactant having no more than 3% peroxide, and at least one buffering agent. In some embodiments, the lyophilization solution further includes at least one bulking agent.

In some embodiments, in the lyophilization solution disclosed herein, disaccharide sugar is present in an amount from 2 to 10% w/v of the lyophilization solution. In other embodiments, the disaccharide sugar is present in an amount from 2 to 8% w/v. In other embodiments, the disaccharide sugar is present in an amount from 2 to 6% w/v. In other embodiments, the disaccharide sugar is present in an amount from 2 to 4% w/v. In other embodiments, the disaccharide sugar is present in an amount from 2 to 3% w/v. In other embodiments, the disaccharide sugar is present in an amount from 2.45 to 2.55% w/v. In some embodiments the disaccharide sugar is chosen from trehalose, lactose, and sucrose. In other embodiments, the disaccharide sugar is sucrose.

In some embodiments, the lyophilization solution disclosed herein includes surfactant. In some embodiments, the surfactant is present in an amount from 0.05 to 1.5% w/v of the lyophilization solution. In other embodiments, the surfactant is present in an amount from 0.07 to 1.5% w/v. In other embodiments, the surfactant is present in an amount from 0.1 to 1.3% w/v. In other embodiments, the surfactant is present in an amount from 0.15 to 1.2% w/v. In other embodiments, the surfactant is present in an amount from 0.25 to 1.0% w/v. In other embodiments, the surfactant is present in an amount from 0.24 to 0.26% w/v. In some embodiments, the surfactant is chosen from polysorbates and poloxamers. In other embodiments, the surfactant is poloxamer 188, poloxamer 168, poloxamer 144, polysorbate 20, polysorbate 60, or polysorbate 80. In other embodiments, the surfactant is polysorbate 80.

The lyophilization solutions disclosed herein are prepared from ultra-purified or super-refined surfactants, which may be obtained commercially. Super refining processes are those that remove impurities (including primary and secondary oxidation products) from an excipient without altering its chemical composition, helping to reduce API interaction and degradation.

In some embodiments, the surfactant has no more than 3%, or 2.5%, or 2%, or 1.5%, or 1% peroxide. Peroxide content is assessed using potentiometric titration according to European Pharmacopeia (EP) 2.5.5, Peroxide value, upon opening the container the first time after being received from the manufacturer. To prevent peroxide formation, in some embodiments, the surfactant is used within 6 months of this testing date and/or within 6 months of receiving it if testing was not completed by the manufacturer, but a low peroxide surfactant was obtained. In some embodiments, the manufacturer may use the container for only one manufacturing procedure instead of being partially used then stored for use in additional lyophilization formulation preparation at a later date.

In some embodiments, the lyophilization solutions disclosed herein include at least one buffering agent. In some embodiments, the buffering agent is chosen from phosphate, arginine, histidine, and Tris HCl. In other embodiments, the buffering agent is Tris HCl. In some embodiments, at least one 5 to 25 mM buffering agent is added. In other embodiments, at least one 5 to 15 mM buffering agent is added. In other embodiments, at least one 7 to 12 mM buffering agent is added. In other embodiments, at least one 9 to 11 mM buffering agent is added. In other embodiments, at least one 10 mM buffering agent is added.

In some embodiments, the lyophilization solution disclosed herein further include 2 to 10% w/v of at least one bulking agent. In other embodiments, the bulking agent is present in an amount from 2 to 8% w/v. In other embodiments, the bulking agent is present in an amount from 2 to 6% w/v. In other embodiments, the bulking agent is present in an amount from 2 to 4% w/v. In other embodiments, the bulking agent is present in an amount from 2 to 3% w/v. In other embodiments, the bulking agent is present in an amount from 2.45 to 2.55% w/v. In some embodiments, the bulking agent is at least one disaccharide sugar. In some embodiments, the bulking agent is chosen from glycine, maltose, glucose, mannitol, and sorbitol. In some embodiments, the bulking agent is mannitol.

The lyophilization solutions disclosed herein are prepared having a pH from 6.5 to 9. In other embodiments the pH is from 7 to 8.

Embodiments disclosed herein provide a stable pharmaceutically acceptable lyophilization solution in a pharmaceutically acceptable aqueous carrier including 0.5 to 1.5 mg/mL of tagraxofusp; 2 to 10% w/v of at least one disaccharide sugar; 0.05 to 1.5% w/v of at least one surfactant; and 5 to 25 mM of at least one buffering agent, wherein the surfactant has no more than 3% peroxide. In other embodiments, the lyophilization solution disclosed herein further includes 2 to 10% w/v of at least one bulking agent.

In some embodiments, the present disclosure provides a stable pharmaceutically acceptable lyophilization solution in a pharmaceutically acceptable aqueous carrier including 0.5 to 1.5 mg/mL of tagraxofusp; 2 to 10% w/v of sucrose; 0.05 to 1.5% w/v of polysorbate 80; 5 to 25 mM tris HCl; and having a pH from 6.5 to 9; wherein the polysorbate 80 has no more than 3% peroxide. In other embodiments, this pharmaceutically acceptable lyophilization solution further includes 2 to 10% w/v of mannitol.

In some embodiments, the present disclosure provides stable pharmaceutically acceptable lyophilization solution in a pharmaceutically acceptable aqueous carrier including 0.9 to 1.1 mg/mL of tagraxofusp; 2.45 to 2.55% w/v of sucrose; 2.45 to 2.55% w/v of mannitol; 0.24 to 0.26% w/v of polysorbate 80; 9 to 11 mM Tris HCl; and having a pH from 6.5 to 9, wherein the polysorbate 80 has no more than 3% peroxide.

In some embodiments, the present disclosure provides a lyophile prepared from the various pharmaceutical compositions described herein. In some embodiments, the lyophile formulation provides for the required dose of 1 to 1.5 mg on dry weight basis.

In some embodiments, the lyophilized dry product is stable at storage temperatures from 2° C. to 8° C. for at least 24 months. In some embodiments, the lyophilized dry product is stable in storage temperatures from 2° C. to 8° C. for 24 months to 5 years.

In some embodiments, the present disclosure provides a method of preparing a tagraxofusp lyophile including the steps of a) providing the lyophilization solution as disclosed throughout and b) lyophilizing the solution to form a lyophile.

In some embodiments, the lyophilization cycle includes the steps of freezing, annealing, primary drying, and secondary drying.

In some embodiments, the lyophilization cycle occurs at a temperature from −40° C. to 25° C.

In some embodiments, the lyophilization cycle occurs over a period of 3 to 4 days.

In some embodiments, the lyophilization comprises a loading step, at least one freezing step, at least one annealing step, and at least one drying step.

In some embodiments, the lyophilization comprises a loading step, at least two freezing steps, at least two annealing steps, and at least one drying step.

In some embodiments, the lyophilization comprises a loading step, at least two freezing steps, and at least two annealing steps that occur over a period of no more than one day; and at least one drying step that occurs over a period of one to five days.

In some embodiments, the lyophilization comprises the following method:
i. product filled vials are semi-stoppered with elastomeric closures and are loaded onto lyophilization chamber on shelves maintained at 10° C. for pre-chilling;
ii. in a step designated as thermal treatment or annealing, the shelf temperature is lowered from 10° C. to −40° C. in three (3) hours, maintained at −40° C. for one (1) hour, raised to −10° C. in one (1) hour, maintained at −10° C. for one (1) hour, lowered back to −40° C. in one (1) hour and maintained at −40° C. for additional one (1) hour;
iii. following the above steps, the condenser is cooled to −60° C. or below, and the vacuum pumps are primed;
iv. the chamber pressure is then reduced to 0.133 mBar to initiate sublimation of ice, also known as a primary drying step;
v. in a primary drying phase, the shelf temperature is raised to −25° C. from −40° C. in one (1) hour and maintained at this temperature for 40 hours. The shelf temperature is then raised to +25° C. in 14 hours;
vi. following this, in secondary drying phase, the shelf temperature is maintained for additional 23.3 hours to complete the drying cycle;
vii. the chamber is bled to 900 mBar atmosphere with nitrogen and the vials are then fully stoppered under nitrogen and removed from the chamber.

In some embodiments, the present disclosure provides a method of reconstituting a lyophile, the method including the steps of adding the lyophile to a sterile vial; adding a first aqueous medium into the vial to make a reconstituted lyophile; and further diluting the reconstituted lyophile in a second aqueous medium to a dose appropriate for administration for the patient.

In some embodiments of the method of reconstituting a lyophile, the first aqueous medium is water, saline, or dextrose 5% in water. In some embodiments of the method of reconstituting a lyophile, the first aqueous medium is water. In some embodiments of the method of reconstituting a lyophile, the second aqueous medium is water, saline, or dextrose 5% in water. In some embodiments of the method of reconstituting a lyophile, the second aqueous medium is water.

In some embodiments, of the method of reconstituting a lyophile, comprising adding 1.0 to 1.5 mL of the first aqueous medium.

In some embodiments, the present disclosure provides a pharmaceutically acceptable formulation reconstituted in an aqueous medium for intravenous injection including 0.5 to 1.5 mg/mL of tagraxofusp; 2 to 10% w/v of at least one disaccharide sugar; 0.05 to 1.5% w/v of at least one surfactant; and a 5 to 25 mM buffering agent.

In some embodiments, the reconstituted formulation for intravenous injection further includes 2 to 10% w/v of at least one bulking agent. In some embodiments of the reconstituted formulation for intravenous injection, the surfactant is chosen from polysorbates and poloxamers. In other embodiments, the surfactant is poloxamer 188, poloxamer 168, poloxamer 144, polysorbate 20, polysorbate 60, or polysorbate 80. In some embodiments, the surfactant is polysorbate 80.

In some embodiments of the reconstituted formulation for intravenous injection, the disaccharide sugar is chosen from trehalose, lactose, and sucrose. In some embodiments, the disaccharide sugar is sucrose.

In some embodiments of the reconstituted formulation for intravenous injection, the bulking agent is chosen from glycine, maltose, glucose, mannitol, and sorbitol. In some embodiments, the bulking agent is mannitol.

In some embodiments, of the reconstituted formulation for intravenous injection the buffering agent is chosen from phosphate, arginine, histidine, and tris HCl. In some embodiments, the buffering agent is tris HCl.

In some embodiments of the reconstituted formulation for intravenous injection, the pH is from 6.5 to 9. In some embodiments, the pH is from 7 to 8. In some embodiments, the pH is 7.5.

In some embodiments of the reconstituted formulation for intravenous injection, the aqueous medium is water for injection (WFI).

In some embodiments of the reconstituted formulation for intravenous injection, upon dilution into an infusion fluid bag, the reconstituted formulation in the infusion fluid bag is essentially free of particulate matter.

In some embodiments of the reconstituted formulation for intravenous injection, upon dilution into an infusion fluid bag, the reconstituted formulation in the infusion fluid bag is essentially free of particulate matter and further wherein the fluid in the infusion fluid bag includes normal saline or Dextrose 5% (w/v).

In some embodiments, provided herein is a vial containing the stable pharmaceutically acceptable lyophilization solutions disclosed herein. In other embodiments, provided herein, is a vial containing the stable lyophile as disclosed herein. In other embodiments, provided herein, is a vial containing the reconstituted solution comprising the reconstituted lyophile as disclosed herein. In some embodiments, the vial is a 2 mL vial or 3 mL vial.

III. Impurity

While a number of trace impurities are present in tagraxofusp or in tagraxofusp formulations, one impurity is associated with a single oxidation of the drug product. By mass spectroscopy, the intact mass of the oxidation impurity presents as a single peak at +16 Da from tagraxofusp. The impurity is a single peak but peptide mapping shows that it represents several species, each with a single oxidation at one of several sites on the tagraxofusp. The amount of the oxidized species of tagraxofusp increases in forced degradation studies of tagraxofusp using peroxide treatment. The oxidation impurity can be separated from tagraxofusp and other impurities using reversed-phase ultrahigh performance chromatography (RP-UPLC), using, for example, the method disclosed in Example 2. In RP-UPLC, the oxidation impurity elutes before tagraxofusp elutes. The oxidation impurity peak on the RP-UPLC chromatogram is the prominent impurity peak closest to the tagraxofusp peak.

Without wishing to be bound to any particular theory, it is believed that the peroxide levels in commercial surfactants contribute to the amount of oxidation impurity found in tagraxofusp or in tagraxofusp formulations.

In some embodiments, the present disclosure provides a lyophile wherein an oxidized species of tagraxofusp is at or below 2%, or is at or below 1% as determined by reversed-phase ultrahigh performance chromatography (RP-UPLC). In other embodiments, an oxidized species of tagraxofusp is at or below 2% as determined by reversed-phase ultrahigh performance chromatography (RP-UPLC) for at least 24 months. In other embodiments, an oxidized species of tagraxofusp is at or below 2% as determined by reversed-phase ultrahigh performance chromatography (RP-UPLC) for at least 12, 18, 24 or 36 months. In other embodiments, an oxidized species of tagraxofusp is at or below 2% as determined by reversed-phase ultrahigh performance chromatography (RP-UPLC) for 12, 18, 24 or 36 months.

In some embodiments, the relative percent abundance of an oxidized species of tagraxofusp in the lyophile increase to no more than 2%, or to no more than 1% over 12 to 36 months, or over 18 to 24 months.

In some embodiments, the relative percent abundance of an oxidized species of tagraxofusp in the lyophile will vary less than the relative percent abundance of the oxidized species of tagraxofusp a liquid drug product formulation over 18, 24 or 36 months.

In some embodiments, the present disclosure provides a stable lyophile including 1.0 mg tagraxofusp; 25 mg of at least one disaccharide sugar; 2.5 mg of at least one surfactant; and 2.4 mg of at least one buffering agent, wherein, the lyophile has no more than 0.03 mg, or 0.02 mg, or 0.01 mg oxidation impurity as determined by reversed-phase ultrahigh performance chromatography (RP-UPLC) for at least 24 months. In some embodiments, the lyophile further includes 25 mg of at least one bulking agent.

IV. Methods of Treatment

In some embodiments, the present disclosure provides a method for treating blastic plasmacytoid dendritic cell neoplasm (BPDCN) including administering to a subject in need thereof an effective amount of the reconstituted formulation for intravenous injection.

In some embodiments, the present disclosure provides a method for treating or inhibiting a myeloproliferative neoplasm (MPN), including administering to a subject in need thereof an effective amount of the reconstituted formulation for intravenous injection. In some embodiments, the present disclosure provides a method for inhibiting or treating myeloproliferative neoplasm presenting with or developing monocytosis including administering to a subject in need thereof an effective amount of the reconstituted formulation for intravenous injection. In some embodiments, the MPN is polycythemia vera (PV), essential thrombocythemia (ET), myelofibrosis (MF), chronic myelomonocytic leukemia (CMML), chronic neutrophilic leukemia, chronic eosinophilic leukemia, systemic mastocytosis (SM), symptomatic hypereosinophilic disorder, or other bone marrow disorder that causes the production of excess red blood cells, white blood cells, and/or platelets, or a primary eosinophilic disorder (PED).

In some embodiments, the present disclosure provides a method for treating or inhibiting acute myeloid leukemia (AML), including administering to a subject in need thereof an effective amount of the reconstituted formulation for intravenous injection.

In some embodiments, the present disclosure provides a method for treating or inhibiting chronic myelomonocytic leukemia (CMML) including administering to a subject in need thereof an effective amount of the reconstituted formulation for intravenous injection.

In some embodiments, the present disclosure provides a method for treating or inhibiting myelodysplastic syndrome (MDS) including administering to a subject in need thereof an effective amount of the reconstituted formulation for intravenous injection.

In some embodiments, the present disclosure provides a method for treating or inhibiting multiple myeloma in a subject in need thereof, including administering to the subject in need thereof an effective amount of the reconstituted formulation for intravenous injection.

In some embodiments, the present disclosure provides a method of treating an autoimmune disease including administering to a subject in need thereof an effective amount of the reconstituted formulation for intravenous injection. In some embodiments, the autoimmune disease is chosen from lupus (e.g., systemic lupus erythematosus, cutaneous lupus, discoid lupus), Sjogren's syndrome, inflammatory arthritis, systemic sclerosis (SSc), morphea, psoriasis, lichen planus, dermatomyositis, lichen sclerosus, and cutaneous graft-versus-host disease (GVHD), adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dense deposit disease, essential mixed cryoglobulinemia, fibromyalgia-fibromyositis, glomerulonephritis (e.g., IgA nephropathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, Ménière's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychondritis, polyendocrinopathies, polyglandular syndromes, polymyalgia rheumatica, polymyositis, post-MI, primary agammaglobulinemia, primary biliary cirrhosis, psoriatic arthritis, Raynaud's phenomenon, relapsing polychondritis, Reiter's syndrome, rheumatic heart disease, rheumatoid arthritis, sarcoidosis, stiff-man syndrome, takayasu arteritis, temporal arteritis/giant cell arteritis, ulcerative colitis, urticaria, uveitis, Uveitis Ophthalmia, vasculitides such as dermatitis herpetiformis vasculitis, vitiligo, and Wegener's granulomatosis.

In some embodiments, the present disclosure provides a method for treating or inhibiting solid tumors including administering to a subject in need thereof an effective amount of the reconstituted formulation for intravenous injection. In some embodiments, the solid tumor is a sarcoma, carcinoma, or a lymphoma.

V. Dosages and Cycles/Timing

The therapeutic regimens disclosed herein include administration of a tagraxofusp or pharmaceutical compositions thereof to the subject in need thereof. In general, dosages based on body weight are from 4 µg/kg to 20 µg/kg. In other embodiments, tagraxofusp is administered at a dose of 7 µg/kg to 16 µg/kg. In some embodiments, the tagraxofusp is administered at a dose of 7 µg/kg. In some embodiments, the tagraxofusp is administered at a dose of 9 µg/kg. In some embodiments, the tagraxofusp is administered at a dose of 12 µg/kg. In other embodiments the tagraxofusp is administered at a dose of 12 µg/kg over 15 minutes. In other embodiments the tagraxofusp is administered at a dose that is the maximum tolerated dose.

The therapeutic regimens disclosed herein include administration of tagraxofusp or pharmaceutical compositions thereof to the subject in a single dose or in multiple doses (e.g., 2, 3, 4, 5, 6, 7, 8, 10, or more) of from 4 µg/kg to 20 µg/kg. For example, the tagraxofusp is administered at a dose of 1 µg/kg, 4 µg/kg, 7 µg/kg, 8 µg/kg, 9 µg/kg, 12 µg/kg, 16 µg/kg, or 20 µg/kg.

In certain embodiments, the methods of treatment provided herein include administration of tagraxofusp or pharmaceutical compositions thereof in single or multiple doses. When administered in multiple doses, the tagraxofusp or pharmaceutical compositions are administered with a frequency and in an amount sufficient to treat and/or manage the disease being treated. In certain embodiments, the frequency of administration ranges from once a day up to once every eight weeks. In certain embodiments, the conjugate is administered once a day. For example, in certain embodiments, the tagraxofusp is administered once daily at a dose from 4 µg/kg/day to 20 µg/kg/day. For example, the tagraxofusp is administered at a dose of 1 µg/kg/day, 4 µg/kg/day, 7 µg/kg, 8 µg/kg/day, 9 µg/kg, 12 µg/kg/day, 16 µg/kg/day, or 20 µg/kg/day. In a specific embodiment, the tagraxofusp is administered once daily at a dose of 7 µg/kg/day. In a specific embodiment, the tagraxofusp is administered once daily at a dose of 9 µg/kg/day. In a specific embodiment, the tagraxofusp is administered once daily at a dose of 12 µg/kg/day. In a specific embodiment, the tagraxofusp is administered once daily at a dose of 16 µg/kg/day. In certain embodiments, the conjugate is administered more than once a day, for example, twice a day, three times a day, four times a day, five or more times a day.

The per day dosages described herein may be administered on consecutive and/or non-consecutive days. In a specific embodiment, a per day dosage is administered on non-consecutive days throughout a week, e.g., Monday, Wednesday, and Friday. In another specific embodiment, a per day dosage is administered on consecutive days throughout a week, e.g. Monday through Sunday or a fewer number of consecutive days (such as for five days).

In certain embodiments, the tagraxofusp is administered once daily for one or more consecutive days. For example, the tagraxofusp is administered once daily for 1 day, 2 days, 3 days, 4 days, 5 days, 6 days, or 7 days. In some embodiments, the tagraxofusp is administered once every day for 3 days. In other embodiments the tagraxofusp is administered once every day for 5 days. In certain embodiments, the conjugate is administered once a week, twice a week, three times a week, four times a week, five times a week, six times a week, or seven times a week. In certain embodiments, a tagraxofusp is administered at least twice a week (e.g., 2 times, 3 times, 4 times, 5 or more times) in a week or during a treatment cycle.

In certain embodiments, the tagraxofusp is administered in one cycle, for example the treatment cycle is at least one-week long (e.g., 1 week, 2 weeks, 3 weeks, 4 weeks, 5 or more weeks). In certain embodiments, the tagraxofusp is administered for multiple cycles, such that each treatment cycle is at least one-week long (e.g., 1 week, 2 weeks, 3 weeks, 4 weeks, 5 or more weeks). For example, in an embodiment, the administering of the tagraxofusp is repeated by administering the tagraxofusp for multiple treatment cycles of 2 weeks, 3 weeks, 4 weeks, 5 weeks, 6 weeks, 7 weeks, or 8 or more weeks. In certain embodiments, the administering of the tagraxofusp is repeated by administering the tagraxofusp for at least one dose (e.g., 1 dose, 2 doses, 3 doses, 4 doses, 5 doses, 6 doses, or 7 or more doses) per treatment cycle. In certain embodiments, the administering of the tagraxofusp is repeated by administering the tagraxofusp at 1 to 5 (e.g., 1, 2, 3, 4, 5) doses per treatment cycle. In a certain embodiment, the tagraxofusp is administered once daily for 1-5 consecutive days. In other embodiments the tagraxofusp is administered for 5 days during any one of the first 10 days of a 21-day cycle. In other embodiments the tagraxofusp is administered for 3 days during a 21-day cycle. In other embodiments the tagraxofusp is administered for 5 days during a 28-day cycle.

The tagraxofusp may be administered repeatedly for an unlimited number of cycles. For example, in certain embodiments, the tagraxofusp is administered for as many cycles as deemed warranted by the attending physician. In certain embodiments, the tagraxofusp is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more cycles.

In certain embodiments, the dosage of tagraxofusp is administered as an intravenous infusion over, for example, 1, 2, 3, 4, 5, 6, 7, 8, 9, 10, 11, 12, 13, 14, 15, 20, 25, 30, 35, 40, 45, 50, 55, 60, 120, 180, or 240 minutes. In certain embodiments, the tagraxofusp is administered as an intravenous infusion over 15 minutes.

VI. Combination Therapies

The present disclosure also provides methods for treating, and/or managing diseases by administering a therapeutically effective amount of tagraxofusp to the subject and one or more additional therapies. In a specific embodiment, the combination therapies include a pharmaceutical composition in accordance with the present disclosure and at least one other therapy that has the same mechanism of action as said conjugate. In another specific embodiment, the combination therapies include a pharmaceutical composition identified in accordance with the methods of the present disclosure and at least one other therapy (e.g., prophylactic or therapeutic agent), which has a different mechanism of action than said conjugate.

The pharmaceutical compositions disclosed herein and the additional therapy can be administered separately, concurrently, or sequentially. The combination of agents can act additively or synergistically. The combination therapies of the present disclosure may reduce the side effects associated with the therapies (e.g., prophylactic or therapeutic agents).

The therapeutic agents of the combination therapies can be administered to a subject in the same pharmaceutical composition. Alternatively, the therapeutic agents of the combination therapies can be administered concurrently to a subject in separate pharmaceutical compositions. The prophylactic or therapeutic agents may be administered to a subject by the same or different routes of administration.

All numbers recited throughout, are modified by the term about, unless otherwise indicated, and as such include values that are no more than 10% above or below the value being modified.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

It should be understood that the expression "at least one of" includes individually each of the recited objects after the expression and the various combinations of two or more of the recited objects unless otherwise understood from the context and use.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context. The use of any and all examples, or exemplary language herein, for example, "such as," "including," or "for example," is intended merely to better illustrate the present teachings and does not pose a limitation on the scope of the invention unless claimed. No language in the specification should be construed as indicating any non-claimed element as essential to the practice of the present teachings.

The use of the singular herein, for example, "a," "an," or "the," includes the plural (and vice versa) unless specifically stated otherwise.

It should be understood that the order of steps or order for performing certain actions is immaterial so long as the present teachings remain operable. Moreover, two or more steps or actions can be conducted simultaneously.

At various places in the present specification, values are disclosed in groups or in ranges. It is to be understood that such range formats are used merely for convenience and brevity and should be interpreted flexibly. It is specifically intended that the description include each and every individual subcombination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

EXAMPLES

In order that the invention described herein can be more fully understood, the following examples are set forth. It should be understood that these examples are included merely for purposes of illustration of certain aspects and embodiments of the present disclosure and are not to be construed as limiting the invention in any manner. Reasonable variations, such as those that occur to a reasonable artisan, can be made herein without departing from the scope of the present disclosure.

Tagraxofusp is a fusion protein manufactured via fermentation in an *E. coli* construct that has been genetically modified to produce the target protein in inclusion bodies. The tagraxofusp protein is a CD123-directed cytotoxin composed of human IL-3 and truncated diphtheria toxin (DT) fusion protein that targets CD123-expressing cells. It has an N-terminal methionine and the DT portion includes the first 388 amino acids of diphtheria toxin (DT) including the catalytic and translocation domains. The amino acid sequence of tagraxofusp is (SEQ ID NO: 1)
MGADDVVDSSKSFVMENFSSYHGTKPGYVDSIQKGIQKPKSGTQGNYDD

DWKGFYSTDNKYDAAGYSVDNENPLSGKAGGVVKVTYPGLTKVLALKVD

NAETIKKELGLSLTEPLMEQVGTEEFIKRFGDGASRVVLSLPFAEGSSS

VEYINNWEQAKALSVELEINFETRGKRGQDAMYEYMAQACAGNRVRRSV

GSSLSCINLDWDVIRDKTKTKIESLKEHGPIKNKMSESPNKTVSEEKAK

QYLEEFHQTALEHPELSELKTVTGTNPVFAGANYAAWAVNVAQVIDSET

ADNLEKTTAALSILPGIGSVMGIADGAVHHNTEEIVAQSIALSSLMVAQ

AIPLVGELVDIGFAAYNFVESIINLFQVVHNSYNRPAYSPGHKTRPHMA

PMTQTTSLKTSWVNCSNMIDEIITHLKQPPLPLLDFNNLNGEDQDILME

NNLRRPNLEAFNRAVKSLQNASAIESILKNLLPCLPLATAAPTRHPIHI

KDGDWNEFRRKLTFYLKTLENAQAQQTTLSLAIF.

Example 1: Baseline Aqueous Formulation

The baseline aqueous formulation of Tagraxofusp for injection was not a lyophilized formulation. This formulation did not show the desired shelf life at the preferred storage temperatures as illustrated in this example.

Tagraxofusp for Injection, 1 mg/mL (1 mL/vial), was provided as a liquid drug product in 2 cc clear, colorless glass vials. The composition of this drug product solution was 1.0 mg/mL Tagraxofusp in 75 mM NaCl (USP, EP), 5% (w/w) sorbitol (USP/NF, EP), and 20 mM Tris buffer (USP, EP) at pH 7.5. Although this formulation was intended to be stable at a refrigerated storage conditions (5±3° C.), upon generation of longer-term stability data it was found that −20° C. storage was beneficial to achieve the desired shelf-life. Stability studies, which included evaluation by a variety of analytical techniques such as reversed phase ultrahigh performance chromatography (RP-UPLC), size exclusion high performance chromatography (SEC-HPLC), sodium dodecyl sulfate polyacrylamide gel electrophoresis (SDS-PAGE), AEX-UPLC and potency by cytotoxicity bioassay, showed that the product started to fall outside the desired acceptance criteria within 12-18 months at 5±3° C., but met all acceptance criteria through 36 months of testing when stored at −20° C., without an appreciable decline in purity or potency.

To obtain the desired shelf life at the preferred storage temperatures, a lyophilized formulation of tagraxofusp was developed. The following Examples 2-5 provide some of the experimental processes and procedures used to arrive at the final improved formulations for lyophilization, and example of which is shown in Example 6.

Example 2: Surfactant Evaluations for Use in Improved Formulations for Lyophilization To address the tendency of the protein to form particulates, particularly at the lower protein concentrations used for dose delivery, a suitable surfactant is added to the formulation as a preventive measure.
Table 1 shows results of the study wherein lyophilized tagraxofusp was added to 50-cc saline infusion bags and agitated for six hours with various amounts of surfactants.

Lyophilization steps were performed as follows: product filled vials were semi-stoppered with elastomeric closures and loaded onto lyophilization chamber on shelves maintained at 10° C. for pre-chilling. In a step designated as thermal treatment or annealing, the shelf temperature was lowered from 10° C. to −40° C. in three (3) hours, maintained at −40° C. for one (1) hour, raised to −10° C. in one (1) hour, maintained at −10° C. for one (1) hour, lowered back to −40° C. in one (1) hour and maintained at −40° C. for additional one (1) hour. Following the above steps, the condenser was cooled to <−60° C. or below, and vacuum pumps were primed. The chamber pressure was then reduced to 0.133 mBar to initiate sublimation of ice, also known as the primary drying step. In the primary drying phase, the shelf temperature was raised to −25° C. from −40° C. in one (1) hour and maintained at this temperature for 40 hours. The shelf temperature was then raised to +25° C. in 14 hours. Following this, in the secondary drying phase, the shelf temperature was maintained for an additional 23.3 hours to complete the drying cycle. Finally, the chamber was bled to atmosphere with nitrogen to 900 mBar and the vials were then fully stoppered under nitrogen and removed from the chamber.

The results showed that a small amount of surfactant was sufficient to prevent aggregation-mediated product losses (as seen by recovery studies using SEC-HPLC) as well as visible particulate formation. Although both polysorbate 80 and poloxamer 188 were able to reduce particulate formation, it was found that polysorbate 80 was able to achieve this at a lower concentration than that of poloxamer 188. Based upon these results, polysorbate 80 was selected as the surfactant and was included in all the subsequent development studies.

TABLE 1A

Effect of Inclusion of Surfactant in Tagraxofusp (1 mg/mL) Solutions

| Surfactant | Amount (% w/v) | Clarity of solution | % Recovery by SEC-HPLC |
|---|---|---|---|
| | | Agitation at 80 RPM for 6 hours | |
| None | — | Hazy, few particles | 79.6 |
| Polysorbate 80 | 0.25 | Clear, no particles | 96.3 |
| | 0.5 | Clear, no particles | 99.8 |
| | 1.0 | Clear, no particles | 98.9 |
| Poloxamer 188 | 0.5 | Clear, no particles | 95.6 |
| | 1.0 | Clear, no particles | 95.3 |
| | 1.5 | Clear, no particles | 96.4 |
| | 2.0 | Clear, no particles | 96.8 |

Studies have shown a correlation between the amount of peroxide in the surfactant with the amount of the impurity identified as an oxidized species of tagraxofusp measured in the Drug Product at release and during stability studies. Higher levels of peroxide in the surfactant, (for example, peroxide value >2 meqO$_2$/kg), lead to higher levels of this impurity in the final drug product, (for example, >1%). Peroxide content of the surfactant was assessed using potentiometric titration according to European Pharmacopeia (EP) 2.5.5, Peroxide value.
Quantification of Oxidized Species of Tagraxofusp by RP-UPLC Reversed phase ultra-performance chromatography (RP-UPLC) was used to determine the purity of the tagraxofusp liquid drug product (DP). The method was performed on a reversed-phase ultra-performance liquid chromatography system (RP-UPLC) using an Agilent Zorbax 300 SB-C3, 2.1×100 mm, 1.8 µm column. The column was eluted using a discontinuous gradient of water and acetonitrile with 0.1% TFA. Detection was by A280. The percent peak area of the main peak and major impurities are reported relative to the total peak area.

Equipment: Liquid chromatography system capable of handling a 1.8 µm particle size reversed phase column with ultraviolet (UV) detector, degassing module, thermostat-controlled column compartment and refrigerated autosampler (e.g., Waters Acquity H-Class UPLC with a 250 µL mixer and a 50 µL injection loop)).

Solutions: Mobile phase A: purified water with 0.1% trifluoroacetic acid (TFA), Mobile phase B: Acetonitrile (ACN) with 0.1% TFA.

Reference Standard and Sample Preparation: Reference material was tested without dilution. The injection volume was calculated to deliver target amount of 4.0 µg. For reference material the target load was 4.0 µg (1.5 mg/mL reference material inject 2.7 µL). Drug Product target load was 4.0 µg (1 mg/mL DP inject 4.0 ul).

Instrument Set-up: Conditions Specific for Analysis (Injection Loop Size: 50 µL)

| Flow | |
|---|---|
| 0.3 | mL/min |

| Solvent Starting Conditions | |
|---|---|
| MPA | 70% |
| MPB | 30% |

| Pressure Limits | | | |
|---|---|---|---|
| Min | 0 psi | Max | 14,000 psi |

| Seal Wash | Seal Wash Period |
|---|---|
| 50% CAN | 5.00 mins |

| Colum Temperature | 45.0 ± 1° C. |
|---|---|

| Time Table | | |
|---|---|---|
| Minutes | MPA (%) | MPB (%) |
| 0 | 70.0 | 30.0 |
| 1.5 | 70.0 | 30.0 |
| 5.5 | 50.0 | 50.0 |
| 19.0 | 23.0 | 77.0 |
| 19.1 | 5.0 | 95.0 |
| 21.5 | 5.0 | 95.0 |
| 21.6 | 70.0 | 30.0 |
| 24.5 | 70.0 | 30.0 |

Sample Set Up: Run sequence for sample analysis

| Vial | Sample Load (µg) | Inj. Vol. (µL) | No. of Inj. | Sample Name | Method | Function | Run Time (Min.) |
|---|---|---|---|---|---|---|---|
| 1 | — | 0 | 2 | No injection | Analysis | Inject immediate sample | 24.5 |
| 1 | — | 4.0 | 1 | Mobile Phase A blank | Analysis | Inject sample | 24.5 |
| 2 | 4.0 | 2.7 | 5 | Initial system suit-reference material | Analysis | Inject control | 24.5 |
| 3-5 | 4.0 | * | 3 | Samples 1-3 | Analysis | Inject sample | 24.5 |
| 2 | 4.0 | 2.7 | 1 | Bracketing system suit | Analysis | Inject control | 24.5 |
| 6-8 | 4.0 | * | 3 | Samples 4-6 | Analysis | Inject sample | 24.5 |
| 2 | 4.0 | 2.7 | 1 | Bracketing system suit | Analysis | Inject control | 24.5 |
| 1 | — | 0 | 1 | No inject | Shutdown | Inject immediate sample | 7 |

*Sample volume determined by calculating a 4.0 µg sample injection load (4 µL for DP at 1.0 mg/mL).

A blank injection followed by 5 injections of the reference standard for system suitability, was performed prior to sample analysis. A bracketing injection of Reference Material (System Suitability) was made after 9 sample injections and following the final sample injection. Each sample was injected in triplicate.

Peak Integration: The identity of the peaks in the samples were confirmed by a comparison to Reference Material injected closest in time. The Main Peak retention time, Impurity 1 RRT, and Impurity 2 RRT for the tagraxofusp Reference Material were within the ranges specified under System Suitability.

System Suitability The reference material chromatograms was visually comparable to an example chromatogram. Bracketing reference material injections had main peak percent purity within ±2.0% of the mean percent purity for the initial 5 reference material system suitability injections. The main peak percent purity CV of the reference material system suitability injections were ≤2%. The USP Theoretical Plates criteria for the main peak of each system suitability injection were ≥11000. The USP tailing of the reference material system suitability injections were ≤2.2. The main peak in the reference material migrated between 13.9 minutes and 16.0 minutes. The RRT for Impurity 1 in the reference material was 0.91-0.92. The RRT for Impurity 2 in the reference material was 0.93-0.95.

Assay Acceptance Criteria: All samples were preceded and followed by a passing bracketing standard. The percent purity column volume (CV) for sample triplicate injections was ≤2% (n=3) for main peak percent purity. The CV for sample triplicate injections was ≤2% (n=3) for main peak retention time.

Figure 1B:
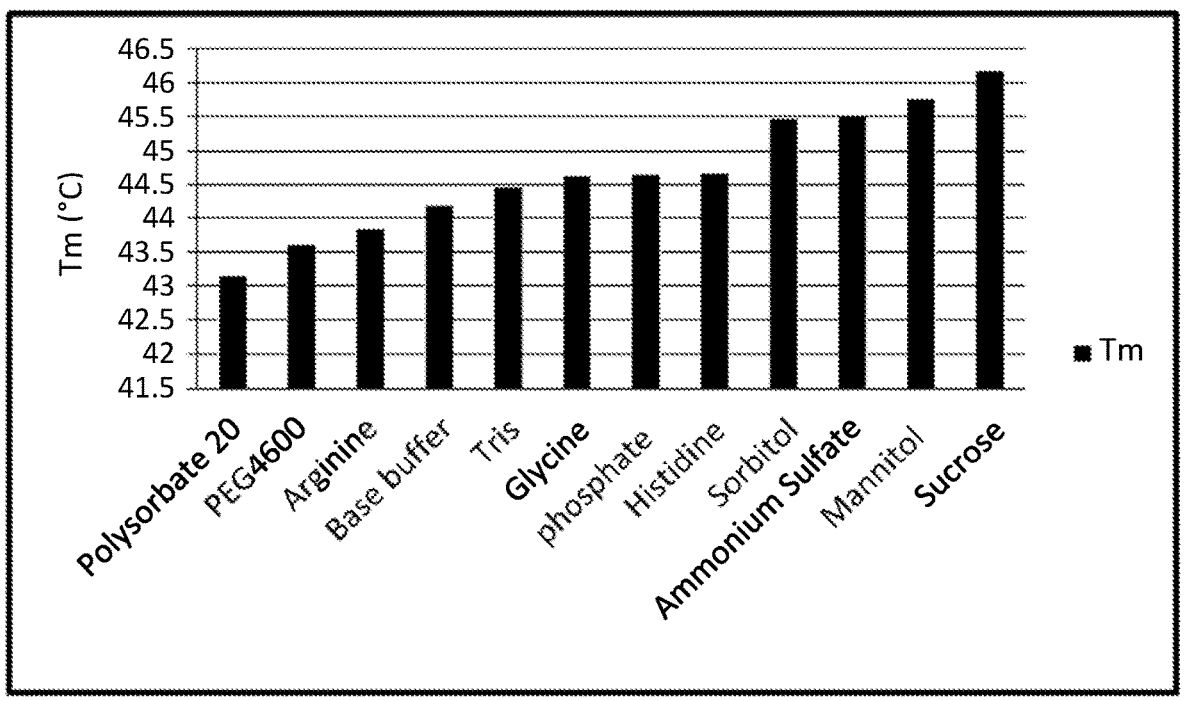
FIG. 1B provides DSC Data from the evaluations of stabilizing excipient detailed in Example 2.

Example 3: Stabilizer Evaluations for Use in Improved Formulations for Lyophilization The thermal stability of tagraxofusp bulk drug substance (BDS) was evaluated in the presence of various Generally Recognized as Safe (GRAS) stabilizers via differential scanning calorimetry (DSC) testing, and it was found that sucrose provided the greatest increase in melting temperature (Tm) among the excipients evaluated. These results are presented in Table 2 and FIG. 1. High Tm values indicate that the excipient offers protection to the tagraxofusp molecule by increasing its denaturation temperature—an indication of stabilizing the molecule to a greater extent. As seen in Table 2, sucrose and mannitol rank highest amongst the excipients evaluated. Sucrose may also serve as a cryoprotectant during the lyophilization process that protects against denaturation during both the freezing and drying stages of the lyophilization cycle. Moreover, mannitol may also serve as a caking agent thereby providing structure to the cake and helping removal of moisture during sublimation and secondary drying process. These studies were run on samples that were not lyophilized.

TABLE 2

DSC Data for Stabilizing Excipient Evaluations

| Buffer # | T ½ | Tm (° C.) |
| --- | --- | --- |
| Sucrose | 5.55 | 46.18 |
| Mannitol | 5.52 | 45.77 |
| Ammonium Sulfate | 4.31 | 45.5 |
| Sorbitol | 5.1 | 45.46 |
| Histidine | 6.8 | 44.66 |
| Phosphate | 6.37 | 44.64 |
| Glycine | 5.11 | 44.62 |
| 20 mM tris pH 7.5 | 5.52 | 44.46 |

TABLE 2-continued

DSC Data for Stabilizing Excipient Evaluations

| Buffer # | T ½ | Tm (° C.) |
| --- | --- | --- |
| Base buffer | 7.24 | 44.18 |
| Arginine | 8.1 | 43.83 |
| PEG4600 | 5.96 | 43.61 |
| Polysorbate 20 (0.034%) | 4.67 | 43.15 |

Example 4: Buffer Evaluations for Improved Formulations for Lyophilization

Four different buffers, suitable for adjustments to the desired pH of 7.5, were evaluated in short-term stability studies of lyophilized tagraxofusp samples. All the formulations were prepared by diafiltration of the bulk drug substance (containing Tris buffer) into 10 mM buffers of either phosphate, arginine, histidine, or Tris buffer at pH 7.5. To these solutions, sucrose (10% w/v) and polysorbate 80 (0.25% w/v) was added. The solutions were filtered through a 0.22 µM low protein binding filter. A volume of 1.1 mL of the filtered solutions was added to 3-cc clean glass vials. The solution-filled vials were semi-stoppered with coated stoppers and placed in the lyophilizer chamber (Model: Epsilon 2-6D by Ima Life, Italy). The lyophilization cycle used was as follows: the shelves were cooled to −40° C. over 3 hours followed by a thermal treatment at −15° C. for one hour. The shelves were then cooled to −45° C. again and the vacuum was initiated. Once the pressure was below 0.133 mBar, primary drying was conducted at a shelf temperature of −30° C. for about 16 hours. The shelf temperature was then raised to 25° C. over 14 hours and maintained at 25° C. for an additional 12 hours during secondary drying. At the end of the cycle, the chamber was bled with dry air and the vials were stoppered inside the chamber. The stoppered vials were unloaded and crimped with aluminum crimp.

The cake quality was evaluated by appearance, and the reconstituted solution was tested for clarity and area percent of tagraxofusp monomer by SEC-HPLC. Testing was performed immediately after lyophilization and after storage at 50° C. for 4 weeks. The results are summarized in Table 3 and show that each buffer performed similarly. Because Tris buffer is also the buffer of the bulk drug substance, using Tris buffer can simplify the manufacturing process. It was therefore selected as the buffer for subsequent studies.

TABLE 3

Evaluation of Various Buffer Types in Lyophilization of Tagraxofusp Formulations: Tagraxofusp (1 mg/mL) containing Sucrose 10% (w/v)

| | | Containing Polysorbate 80 (0.25% w/v) | | | |
| --- | --- | --- | --- | --- | --- |
| Test | | PT | AT | HT | TT |
| Cake Appearance | | Intact white to off-white cake | Intact white to off-white cake | Intact white to off-white cake | Intact white to off-white cake |
| Reconstitution Time | | <1 minute | <1 minute | <1 minute | <1 minute |
| Clarity of solution | | Clear, colorless solution; no visible particles | | | |
| % monomer by SEC-HPLC | Pre-Lyo | 97.68 | 98.44 | 95.26 | 97.99 |
| | Post-Lyo | 92.14 | 97.16 | 95.25 | 97.88 |
| | Post-Lyo (4 wk @, 50° C.) | 96.54 | 97.43 | 96.83 | 94.88 |

PT = Phosphate buffer with polysorbate 80,
AT = Arginine buffer with polysorbate 80
HT = Histidine buffer with polysorbate 80,
TT = Tris buffer with polysorbate 80

Example 5: Bulking Agent Evaluations for Improved Formulations for Lyophilization Initial lyophilization studies performed in a laboratory scale lyophilizer utilizing sucrose (10% w/v) as a bulking agent/stabilizer yielded good cakes and showed acceptable stability of lyophilized tagraxofusp. However, upon scale-up studies on a larger scale lyophilizer unit, it was observed that the cake appearance was not consistently acceptable and resulted in rejections due to issues such as shrinkage. To address this, additional lyophilization experiments were performed in the laboratory wherein another commonly used excipient in injectable products, mannitol, was used as a bulking agent along with sucrose. The purpose of mannitol was to provide a firmer cake structure that ensured no shrinkage of the cake while sucrose acted as an amorphous cryo/lyoprotectant during the lyophilization process to protect the protein from freezing and/or dehydration stresses.

After the formulation was revised to include mannitol as the bulking agent, additional lyophilization experiments were performed to identify the amount of surfactant necessary to ensure control of particulates in the new mannitol/sucrose matrix. The dried samples were evaluated for cake appearance, reconstitution time, pH, appearance after reconstitution, percent monomer by RP-HPLC and residual moisture by Karl Fischer analysis. The results of these studies are summarized in Table 4, which concluded that the polysorbate 80 surfactant at the level of 0.25% w/v was still appropriate for acceptable stability of tagraxofusp lyophilized drug product for up to 11 months at room temperature storage.

TABLE 4

Effect of the Amount of the Surfactant in the Tagraxofusp Lyophilized Formulation. Other Excipients: Sucrose 2.5% (w/v) and Mannitol 2.5% (w/v) in Tris buffer

| # | Amount of Polysorbate 80 (% w/v) | Cake Appearance | Recon. Time (Sec) | Reconstituted Solution Appearance | pH | % Monomer by RP-HPLC* | Moisture by KF (%) |
|---|---|---|---|---|---|---|---|
| 1 | 0.0 | Good | 10 | Hazy, visible particles | 7.36 | 98.5 | 2.3 |
| 2 | 0.1 | Good | 8 | Clear, no visible particles | 7.37 | 96.5 | 2 |
| 3 | 0.25 | Good | 10 | Clear, no visible particles | 7.35 | 94.1 | 1.7 |
| 4 | 0.5 | Good | 11 | Clear, no visible particles | 7.4 | 87.2 | 1.5 |
| 5 | 1.0 | Good | 8 | Clear, no visible particles | 7.43 | 84.1 | 1.8 |

*After storage at room temperature for approximately 11 months.

Example 6: Final Composition of the Solution for Lyophilization

Based upon the above results and the confirmatory results from formulation development runs, the formulation of the tagraxofusp solution for lyophilization (1 mg/mL) was recommended for the proposed clinical studies as shown in Table 5. For the 1.5 mg presentation, the formulation was scaled consistently for all materials. The table lists the composition of the solution for lyophilization as well as the rationale for the addition of each component.

TABLE 5

Proposed Composition for Lyophilization of Tagraxofusp

| Ingredient | Rationale for use | Amount/ 1 mg/vial* | Amount/1.5 mg/vial* |
|---|---|---|---|
| SL-401 | Active | 1.0 mg | 1.5 mg |
| Sucrose, NF/EP | Cryo/Lyoprotectant | 25 mg | 37.5 mg |
| Mannitol, USP/EP | Bulking agent | 25 mg | 37.5 mg |
| Polysorbate 80, NF, EP | Surfactant | 2.5 mg | 3.75 mg |
| Tromethamine, USP/EP | Buffer | 2.4 mg | 3.6 mg |
| Hydrochloric acid, NF/EP (as 1N solution) | pH adjustment | QS for pH | QS for pH |
| Sodium Hydroxide, NF/EP (as 1N solution) | pH adjustment | QS for pH | QS for pH |
| Water for injection, USP** | Vehicle | QS to target weight | QS to target weight |

*This amount is not inclusive of the 4% overfill by weight
**Removed during lyophilization Physicochemical and Biological Properties:

The drug product pH was set at 7.5, which is near the physiological pH of 7.4, and is consistent with the pH of both the drug substance (DS) and the prior liquid drug product formulation. This pH provides security against the known physical instability/loss of activity (potency) of the DS at pH below 6.5. When the lyophile is reconstituted with Water for injection (WFI), it delivers a clear colorless liquid containing 1 mg/mL of tagraxofusp and is essentially free of particulates. The presence of a low level of surfactant prevents protein aggregation, which is a known attribute of the DS at lower dilutions such as those used for infusion.

The following is an example of one manufacturing procedure for the formulations disclosed herein.

Example 7: Manufacturing of Tagraxofusp for Injection

A manufacturing process for tagraxofusp for Injection, 1 mg/vial, consists of the following standard unit operations: compounding of the solution for lyophilization, filtration through sterilizing grade 0.22 μm filters, filling of the filtered sterile solution into glass vials, and lyophilization of filled vials to obtain the final drug product cake.

Compounding:

The formulation of the lyophilized product was established as outlined herein above. In-process specifications were established to verify the pH, density and tagraxofusp concentration of the formulated drug product solution prior to proceeding to sterile operations.

Sterilization through 0.22 μm Membrane Filters:

Tagraxofusp for Injection bulk solution cannot be terminally sterilized due to the heat sensitivity of the protein molecule, consistent with all protein therapeutics. As such, a standard sterile filtration operation was designed to perform sterilization of the compounded bulk solution by membrane filtration through one 0.45 μm pre-filtration sterile filter and then through two 0.22 μm hydrophilic polyvinylidene fluoride (PVDF) membranes contained in a polycarbonate housing. The compounded bulk passes through the two sterilizing membranes in series, as is typical in sterile filtration operations, to provide redundant sterilizing capability.

Aseptic Filling of the Sterile Solution:

The vial and stopper combination selected for tagraxofusp for Injection had previously been qualified on the manufacturing line at a contract manufacturer. For each vial, 1.04 mL (1.06 grams) or 1.56 mL (1.59 grams) of the membrane filtered tagraxofusp sterile solution is filled into Type I, de-pyrogenated glass vials and the vials are semi-stoppered with sterile rubber closures. The filled vials are then transferred onto the shelves of the lyophilizer chamber for lyophilization.

Overfill:

The clinical drug product has a label claim of either 1 mg/vial and a target fill of 1.06 gm (1.04 mL) per vial or 1.5 mg/vial and a target fill of 1.59 gm (1.56 mL) per vial. The 4% overfill of tagraxofusp is included in each vial to account for the cake displacement during reconstitution and to ensure that the product concentration is exactly 1.0 mg/mL after reconstitution with 1.0 mL/1.5 mL of WFI during dosage preparation. This overfill allows accurate dose preparation on a dose/kg basis.

Lyophilization Cycle Development:

The main excipients of the solution for tagraxofusp for Injection, sucrose and mannitol are at 25 mg/mL each, and thus are present in considerably higher amounts compared to the active component, which is present at 1 mg/mL. The thermal properties of the frozen solution, therefore, are dictated largely by the properties of these two components in the frozen state. The freezing behavior of the tagraxofusp solution for lyophilization by differential scanning calorimetry (DSC) has shown a minor endothermic event at around 32° C. The lyophilization parameters during the primary drying were chosen such that the product temperature remains below −32° C. during the sublimation phase of the drying. A thermal treatment step during freezing is included at −15° C. for approximately 1 hour to ensure complete crystallization of the mannitol and other metastable phases. Upon completion of the primary (sublimation) drying, the shelf temperature is raised to 25° C. and maintained at 25° C. during the rest of the drying cycle to ensure that the secondary (desorption) drying phase is complete and dry product is obtained with low residual moisture level.

Following a number of experimental trials that used a combination of various shelf temperatures, chamber pressures, and duration periods for each phase, a lyophilization cycle was finalized that consistently yielded well-formed cakes with low residual moistures.

Table 6 summarizes the finalized process parameters for use in the lyophilization for tagraxofusp for Injection. In addition to the cycle parameters discussed above, an added specified loading time and an extended freezing time were included in the final cycle as required for standard operation in the production scale equipment. Upon completion of the lyophilization process, the dried vials are fully stoppered inside the lyophilization chamber, unloaded, sealed with aluminum crimps and then rinsed. The crimped vials are then subjected to 100% visual inspection, quality testing, labeling, and packaging.

TABLE 6

A Lyophilization Cycle for Tagraxofusp for Injection

| Step | Initial Temperature (° C.) | Final Temperature (° C.) | Time (min.) | Vacuum (mBar) | Total Time (Min) |
|---|---|---|---|---|---|
| Loading | 10 | 10 | 1 | Atm | 1 |
| Freezing | 10 | −40 | 180 | Atm | 181 |
|  | −40 | −40 | 60 | Atm | 241 |
|  | −40 | −15 | 60 | Atm | 301 |
|  | −15 | −15 | 60 | Atm | 361 |
|  | −15 | −40 | 60 | Atm | 421 |
|  | −40 | −40 | 60 | Atm | 481 |
| Pull Vacuum/ Evacuate | −40 | −40 | 30 | 0.133 | 511 |
| Primary drying | −40 | −25 | 60 | 0.133 | 571 |
|  | −25 | −25 | 2400 | 0.133 | 2971 |
| Secondary drying | −25 | 25 | 840 | 0.133 | 3811 |
|  | 25 | 25 | 1390 | 0.133 | 5201 |
| Pre-Aeration with nitrogen | 25 | 5 | — | 900 |  |
| Stoppering | 5 | 5 | — | 900 |  |
| Aeration with nitrogen | 5 | 5 | — | Atm |  |
| Storage | 5 | 5 | — | Atm |  |
| Unloading | 5 | 20 | — | Atm |  |

Density of Tagraxofusp Bulk Solution for Lyophilization:

The density of the tagraxofusp bulk solution for lyophilization was determined using the Anton-Paar Density meter at room temperature and was found to be 1.02 g/mL.

Determination of Lyophile Displacement Volume:

The lyophile displacement volume is the volume of re-constituted solution in milliliters, displaced by 1.0 g or 1.5 g of the lyophilized dry material. The displacement volume is required for the determination of overfill necessary to achieve a 1 mg/mL solution upon reconstitution with exactly 1.0 mL or 1.5 mL of WFI. The displacement volume for lyophilized tagraxofusp for Injection was determined by placing 1000 mg of lyophilized material into a 10 mL volumetric flask and then adding 10.0 mL of water. The volume of the solution, in excess of 10.0 mL caused by displacement due to the solid content was then measured. Approximately 0.73 mL of water was found displaced when 1 gm of the lyophilized material was dissolved.

Using this relationship, the displacement value of the lyophilized cake was calculated as follows: the total weight of active pharmaceutical ingredient (API) plus the added excipients per mL of drug product (DP) solution is 55.94 mg. Therefore, for a 1.0 mL fill volume at 1.0 mg/mL tagraxofusp, the displacement value of the dried material will be 0.04 mL resulting in 1.04 mL total volume or 0.96 mg/mL of the active. To account for this discrepancy caused by the displacement volume, one must fill about 1.04 mL or 1.56 mL of the solution to be lyophilized for the 1.0 mg/vial fill and the 1.5 mg/vial fill respectively. The resulting dry product will then contain enough of the tagraxofusp active in the reconstituted solution to deliver the targeted concentration.

What is claimed is:

1. A stable solution in a pharmaceutically acceptable aqueous carrier comprising:
   0.5 to 1.5 mg/mL of tagraxofusp;
   2 to 10% w/v of sucrose;
   0.05 to 1.5% w/v of polysorbate 80;
   5 to 25 mM Tris HCl; and
   having a pH from 6.5-9.0
wherein the polysorbate 80 has no more than 3% peroxide.

2. The stable solution of claim 1, further comprising 2 to 10% w/v of at least one bulking agent.

3. The stable solution of claim 2, wherein the bulking agent is present in an amount from 2 to 8% w/v.

4. The stable solution of claim 2, wherein the bulking agent is chosen from glycine, maltose, glucose, mannitol, and sorbitol.

5. The stable solution of claim 4, wherein the bulking agent is mannitol.

6. The stable solution of claim 2, wherein the bulking agent is present in an amount 2 to 4% w/v.

7. The stable solution of claim 1, comprising 0.7 to 1.3 mg/mL of tagraxofusp.

8. The stable solution of claim 1, wherein the polysorbate 80 is present in an amount from 0.1 to 1.3% w/v.

9. The stable solution of claim 1, wherein the sucrose is present in an amount from 2 to 6% w/v.

10. The stable solution of claim 1, wherein the pH is from 6.5 to 8, or wherein the pH is from 7 to 8.

11. The stable solution of claim 1 comprising:
    1 mg/mL of tagraxofusp;
    2.45 to 2.55% w/v of sucrose;
    2.45 to 2.55% w/v of mannitol;
    0.24 to 0.26% w/v of polysorbate 80;
    5 to 25 mM Tris HCl; and
    having a pH from 6.5 to 9,
wherein the polysorbate 80 has no more than 3% peroxide.

12. The stable solution of claim 11, wherein the stable solution is frozen.

13. The stable solution of claim 11, wherein the stable solution is at a temperature of less than 0° C.

14. The stable solution of claim 1, wherein the stable solution is frozen.

15. The stable solution of claim 1, wherein the stable solution is at a temperature of less than 0° C.

16. The stable solution of claim 1, which upon dilution into an infusion fluid bag provides a fluid in the infusion fluid bag that is substantially free of particulate matter.

17. A formulation for intravenous injection comprising 1 part of the stable solution of claim 1 to 50 parts water for injection in an infusion fluid bag.

18. The formulation for intravenous injection of claim 17, wherein the water for injection in the infusion fluid bag includes normal saline or Dextrose 5% (w/v).

19. The formulation for intravenous injection of claim 17, wherein the formulation has no visible particles.

20. A vial containing the stable solution of claim 1.

21. The vial of claim 20, wherein the vial is a 2 mL or a 3 mL vial.

22. The stable solution of claim 1, comprising 0.8 to 1.2 mg/mL of tagraxofusp.

23. The stable solution of claim 1, comprising 1 mg/mL of tagraxofusp.

24. The stable solution of claim 1, wherein the polysorbate 80 is present in an amount from 0.15 to 1.2% w/v.

25. The stable solution of claim 1, wherein the polysorbate 80 is present in an amount from 0.24 to 0.26% w/v.

26. The stable solution of claim 1, wherein the sucrose is present in an amount from 2 to 3% w/v.

27. The stable solution of claim 1, wherein the sucrose is present in an amount from 2.45 to 2.55% w/v.

28. The stable solution of claim 1, wherein the stable solution has no visible particles.

* * * * *